(12) United States Patent
Zhang et al.

(10) Patent No.: US 11,575,089 B2
(45) Date of Patent: Feb. 7, 2023

(54) COMPOUND, DISPLAY PANEL AND DISPLAY APPARATUS

(71) Applicants: WUHAN TIANMA MICROELECTRONICS CO., LTD., Wuhan (CN); WUHAN TIANMA MICROELECTRONICS CO., LTD. SHANGHAI BRANCH, Shanghai (CN)

(72) Inventors: Lei Zhang, Shanghai (CN); Wei Gao, Shanghai (CN); Jinghua Niu, Shanghai (CN); Wenpeng Dai, Shanghai (CN); Yan Lu, Shanghai (CN)

(73) Assignees: WUHAN TIANMA MICROELECTRONICS CO., LTD., Wuhan (CN); Wuhan Tianma Microelectronics Co., Ltd. Shanghai Branch, Shanghai (CN)

( * ) Notice: Subject to any disclaimer, the term of this patent is extended or adjusted under 35 U.S.C. 154(b) by 486 days.

(21) Appl. No.: 16/669,365

(22) Filed: Oct. 30, 2019

(65) Prior Publication Data
US 2020/0373501 A1 Nov. 26, 2020

(30) Foreign Application Priority Data
May 24, 2019 (CN) .......................... 201910439669.3

(51) Int. Cl.
*H01L 51/00* (2006.01)
*C07D 401/14* (2006.01)
*C07D 471/04* (2006.01)
*C09K 11/06* (2006.01)
*H01L 51/50* (2006.01)

(52) U.S. Cl.
CPC ........ *H01L 51/0072* (2013.01); *C07D 401/14* (2013.01); *C07D 471/04* (2013.01); *C09K 11/06* (2013.01); *H01L 51/0067* (2013.01); *C09K 2211/1018* (2013.01); *H01L 51/5072* (2013.01); *H01L 51/5092* (2013.01); *H01L 2251/552* (2013.01)

(58) Field of Classification Search
CPC ............. H01L 51/0072; H01L 51/0067; H01L 51/5072; H01L 51/5092; H01L 2251/552; H01L 51/5004; H01L 51/5076; H01L 51/50; H01L 51/5056; H01L 51/506; C07D 401/14; C07D 471/04; C07D 221/10; C09K 11/06; C09K 2211/1018; C09K 2211/1007; C09K 2211/1011; C09K 2211/1029

USPC .......................................................... 428/690
See application file for complete search history.

(56) References Cited

U.S. PATENT DOCUMENTS

| 2018/0006243 A1* | 1/2018 | Yoo ..................... H01L 51/0054 |
| 2018/0166647 A1* | 6/2018 | Shin .................... H01L 51/5092 |

FOREIGN PATENT DOCUMENTS

| CN | 107556307 A | 1/2018 |
| CN | 108218858 A | 6/2018 |
| CN | 108409730 A | 8/2018 |
| KR | 10-2015-0030294 A | 3/2015 |
| KR | 10-2019-0009704 A | 1/2019 |
| WO | 2018199466 A1 | 11/2018 |

OTHER PUBLICATIONS

Office Action dated Jul. 17, 2020, for Chinese Patent Application No. 201910439669.3. (with English translation, 15 pages).
First Office Action dated Jan. 10, 2020, for Chinese Patent Application No. 201910439669.3. (with English Translation, 21 pages).
Nair, Neelima V. et al., "The synthesis, photophysical properties and water oxidation studies of a series of novel photosensitizer-catalyst assemblies," Inorganica Chimica Acta, 454:27-39, 2017. (13 pages).
Hossain, Md. Delwar et al., "A Heterometallo-Supramolecular Polymer with CuI and FeII Ions Introduced Alternately," European Journal of Inorganic Chemistry, p. 3763-3770, 2014. (8 pages).
Baranoff, Etienne et al., "A pseudo-rotaxane based on an iridium(III)-copper(I) dyad," New Journal of Chemistry, 28:1091-1095, 2004. (5 pages).

* cited by examiner

*Primary Examiner* — Douglas J McGinty
(74) *Attorney, Agent, or Firm* — Christensen O'Connor Johnson Kindness PLLC

(57) ABSTRACT

The present disclosure belongs to the technical field of organic light-emitting diods (OLEDs), and provides a compound used as an electron transmission material of OLEDs. Molecules of the compounds include an aromatic ring (or aromatic fused ring) and a phenanthroline group that are connected to each other. In an embodiment, the compound according to the present disclosure includes two types of groups, i.e., an aromatic ring (or aromatic fused ring) and a phenanthroline (or benzoquinoline) group. These two groups not only have good electron accepting ability, but also can be well doped with metals. The planarity of the two groups is conducive to the stacking of molecules, which facilitates the combination of holes and electrons and generates excitons, thereby increasing the electron mobility of the material and improving efficiency of device.

13 Claims, 2 Drawing Sheets

ET003

COMPOUND, DISPLAY PANEL AND DISPLAY APPARATUS

CROSS-REFERENCE TO RELATED APPLICATIONS

The present application claims priority to Chinese Patent Application No. 201910439669.3, filed on May 24, 2019, the content of which is incorporated herein by reference in its entirety.

TECHNICAL FIELD

The present disclosure relates to the technical field of organic light-emitting diodes (OLEDs), and particularly, to a compound for use as an electron transmission material, such as in a display panel and a display apparatus that include the compound.

BACKGROUND

The electron transmission material used in the conventional electroluminescent device is Alq3, but the electron mobility of Alq3 is relatively low (about $10^{-6}$ cm$^2$/Vs), resulting in an imbalance between electron transmission and hole transmission of the device. With the increasing commercialization and practical application of electroluminescent devices, it is urgent to develop an electron transmission material having higher transmission efficiency and usability. In this field, researchers have made a huge amount of research.

The common electron transmission materials on the market, such as bathphenanthroline (BPhen), bathocuproine (BCP) and 3,3'-[5'-[3-(3-Pyridinyl)phenyl][1,1':3',1''-terphenyl]-3,3''-diyl]bispyridine (TmPyPB), generally meet the market demand for organic electroluminescent panels, but have relatively low glass transition temperature, typically below 85° C. When the device is in operation, generated Joule heat causes molecular degradation and molecular structure changes, resulting in reduced panel efficiency and poor thermal stability. Meanwhile, the molecular structures of such conventional electron transmission materials are highly symmetrical and easily crystallized after a long period of operation. Once the electron transmission material crystallizes, the charge transition mechanism between the molecules is different from the mechanism of normal operation of the amorphous film, resulting in a decrease in the performance of electron transmission and an imbalance of electron and hole mobility of the entire device. Therefore, exciton formation efficiency is greatly reduced. Moreover, the exciton formation occurs at relatively high concentrations at the interface between the electron transmission layer and the light-emitting layer, resulting in a serious decrease in device efficiency and service time.

Therefore, in order to reduce threshold voltage, improve device efficiency, and prolong the device service time, it is urgent to design and develop a stable and efficient electron transmission material and/or electron injecting material, which simultaneously have high electron mobilities, high glass transition temperatures, and effectively doping with metal Yb or Liq$_3$.

SUMMARY

In view of above, the present disclosure provides a compound for use as an electron transmission material having a general structure according to [Chemical Formula 1]:

[Chemical Formula 1]

wherein A has a structure according to [Chemical Formula 2]:

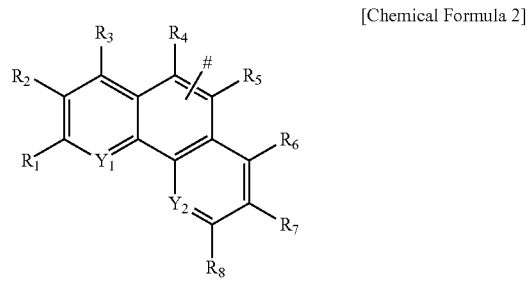

[Chemical Formula 2]

B has a structure according to [Chemical Formula 3-1] or [Chemical Formula 3-2]:

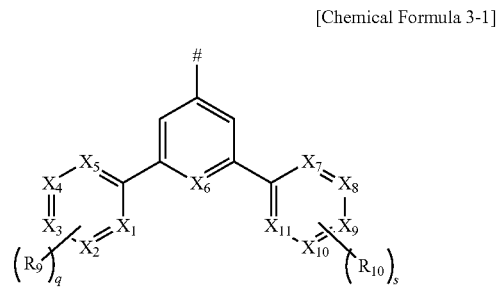

[Chemical Formula 3-1]

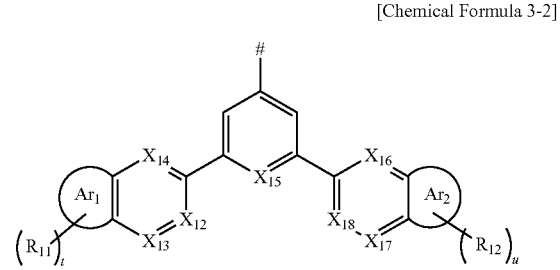

[Chemical Formula 3-2]

L is selected from the group consisting of a substituted or unsubstituted C6 to C30 arylene, and a substituted or unsubstituted C5 to C30 heteroarylene;

q, s, t and u are each an integer independently selected from 1 and 2;

m, n and p are each an integer independently selected from 1 and 2;

$Y_1$ and $Y_2$ are each independently a carbon atom or a nitrogen atom, and at least one of $Y_1$ and $Y_2$ is a nitrogen atom; and at least one of $R_1$ to $R_8$ is a hydrogen atom, and a position where the at least one of $R_1$ to $R_8$ is a hydrogen atom serves as a bonding position to L;

$R_1$-$R_{12}$ are each independently selected from the group consisting of hydrogen, a substituted or unsubstituted C6 to C18 aryl, a substituted or unsubstituted pyridyl, a substituted or unsubstituted quinolyl, a substituted or unsubstituted C1 to C16 alkyl, a substituted or unsubstituted C1 to C16 alkoxy, hydroxyl, and carboxyl;

$X_1$-$X_{11}$ are each independently a carbon atom or a nitrogen atom, at least one of $X_1$-$X_5$ is a nitrogen atom, and at least one of $X_7$-$X_{11}$ is a nitrogen atom;

$X_{12}$-$X_{18}$ are each independently a carbon atom or a nitrogen atom, at least one of $X_{12}$-$X_{14}$ is a nitrogen atom, at least one of $X_{16}$-$X_{18}$ is a nitrogen atom; and $Ar_1$ and $Ar_2$ are each a fused benzene ring; and \# indicates a bonding position.

The present disclosure further provides a display panel, including an organic light-emitting device. The organic light-emitting device includes an anode, a cathode opposite to the anode, an electron transmission layer and a light-emitting layer that are disposed between the anode and the cathode, wherein a material of the electron transmission layer comprises one or more of compounds according to the present disclosure.

The present disclosure further provides a display apparatus, including the display panel according to the present disclosure.

DESCRIPTION OF EMBODIMENTS

Figure 1:
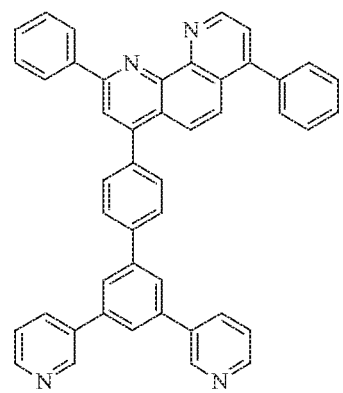
FIG. 1 illustrates a chemical structure of an exemplary Compound ET003 according to an embodiment of the present disclosure.

The present disclosure is further described in the following examples and comparative examples, which are merely intended to illustrate the invention, but not to limit the present disclosure. Any modifications or equivalent substitutions of the technical solutions according to the present disclosure shall fall within the protection scope of the present disclosure.

In an aspect of the present disclosure provides a compound suitable for use as an electron transmission material having a general structure according to [Chemical Formula 1]:

[Chemical Formula 1]

wherein A has a structure according to [Chemical Formula 2]:

[Chemical Formula 2]
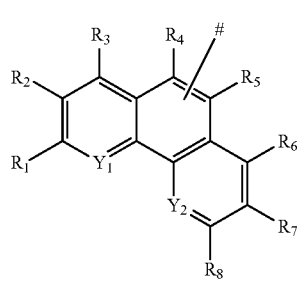

B has a structure according to [Chemical Formula 3-1] or [Chemical Formula 3-2]:

[Chemical Formula 3-1]
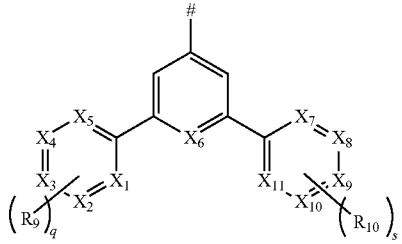

[Chemical Formula 3-2]
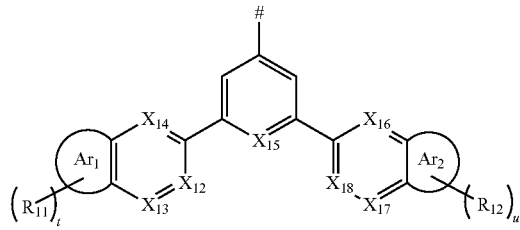

L is selected from the group consisting of a substituted or unsubstituted C6 to C30 arylene, and a substituted or unsubstituted C5 to C30 heteroarylene;

q, s, t and u are each an integer independently selected from 1 or 2;

m, n and p are each an integer independently selected from 1 or 2;

$Y_1$ and $Y_2$ are each independently a carbon atom or a nitrogen atom, at least one of $Y_1$ and $Y_2$ is a nitrogen atom; at least one of $R_1$ to $R_8$ is a hydrogen atom, and a position where the at least one of $R_1$ to $R_8$ is a hydrogen atom serves as a bonding position to L;

$R_1$-$R_{12}$ are each independently selected from the group consisting of hydrogen, a substituted or unsubstituted C6 to C18 aryl, a substituted or unsubstituted pyridyl, a substituted or unsubstituted quinolyl, a substituted or unsubstituted C1 to C16 alkyl, a substituted or unsubstituted C1 to C16 alkoxy, hydroxyl, and carboxyl;

$X_1$-$X_{11}$ are each independently a carbon atom or a nitrogen atom, and at least one of $X_1$-$X_5$ is a nitrogen atom, and at least one of $X_7$-$X_{11}$ is a nitrogen atom;

$X_{12}$-$X_{18}$ are each independently a carbon atom or a nitrogen atom, at least one of $X_{12}$-$X_{14}$ is a nitrogen atom, at least one of $X_{16}$-$X_{18}$ is a nitrogen atom; and $Ar_1$ and $Ar_2$ are each a fused benzene ring; and \# indicates a bonding position.

In an embodiment, the compounds of the present disclosure include a phenanthroline group and an aromatic heterocyclic group such that the compound has a highest occupied molecular orbital (HOMO) value and a lowest unoccupied molecular orbital (LUMO) value that suitably match adjacent functional layers, thereby enhancing the ability of electron injection and transmission. In addition, the compounds of the present disclosure have a wide band gap, such that the material has a higher triplet ET. The groups of the compounds of the present disclosure have a greater conjugation degree and a higher overlapping degree of orbitals, so that the material has high electron mobility and is suitable for use as an electron transmission material in OLEDs.

According to an embodiment of the present disclosure, A has a structure according to [Chemical Formula 2-1]:

[Chemical Formula 2-1]

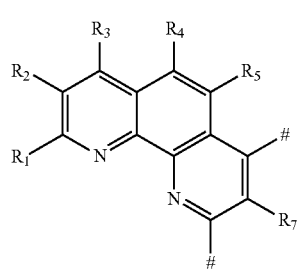

in which # indicates a bonding position.

Phenanthroline has a rigid structure, which is conducive to increasing the glass transition temperature of the material. In addition, the phenanthroline structure is an excellent electron-deficient planar group, which is advantageous for stacking and electronic coupling of molecules, thereby improving the electron mobility of materials. In this regard, the compounds comprising phenanthroline are suitable for use as an electron transmission material for OLEDs. The nitrogen atom in the phenanthroline has a lone pair of electrons, which is conducive to forming a doping system including molecules of the electron transmission material and the metal ions. In addition, the structure of the phenanthroline has asymmetry, which results in an amorphous film morphology of the electron transmission material, improving the feasibility of vapor deposition, and at the same time avoiding a degradation or attenuation of the compound induced by light scattering or crystallization.

According to an embodiment of the present disclosure, A has a structure according to [Chemical Formula 2-2]:

[Chemical Formula 2-2]

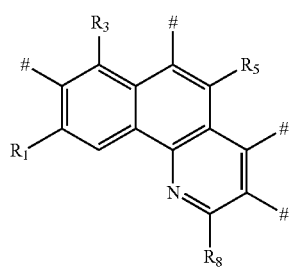

in which # indicates a bonding position.

In the above chemical formula [2-2], the pyridonaphthalene structure endows the molecule with a good rigid structure, and in the meantime, the pyridinium structure has an asymmetry, which is conducive to increasing the glass transition temperature of the material and avoiding a decrease in electron transmission performance caused by crystallization after a long-term operation of the compound molecules. Therefore, the structure can extend the service life of the organic light-emitting device. In addition, the pyridonaphthalene structure is an electron-deficient planar group, which is excellent at stacking and electron coupling of molecules, thereby improving the electron mobility of materials. Therefore, the structure is very suitable for use as an electron transmission material.

According to an embodiment of the present disclosure, L is according to any one of the following formulas:

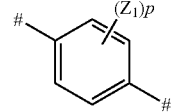
Chemical Formula 2-1

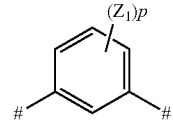
Chemical Formula 2-2

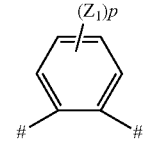
Chemical Formula 2-3

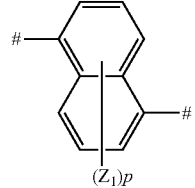
Chemical Formula 2-4

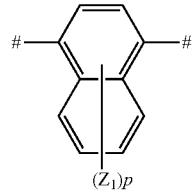
Chemical Formula 2-5

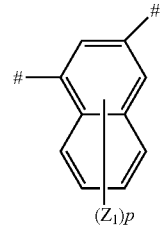
Chemical Formula 2-6

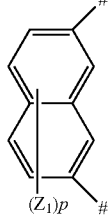
Chemical Formula 2-7

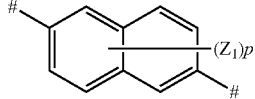
Chemical Formula 2-8

-continued

Chemical Formula 2-9
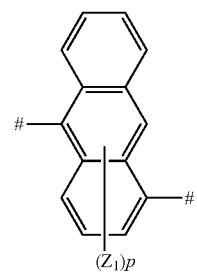

Chemical Formula 2-10
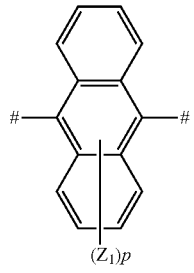

Chemical Formula 2-11
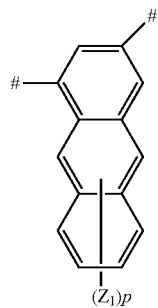

Chemical Formula 2-12
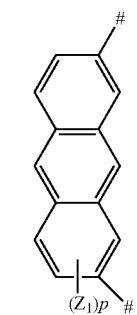

Chemical Formula 2-13
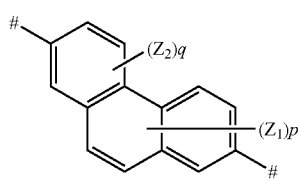

Chemical Formula 2-14
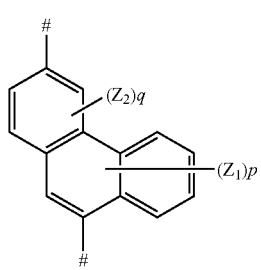

-continued

Chemical Formula 2-15
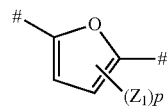

Chemical Formula 2-16
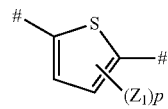

Chemical Formula 2-17
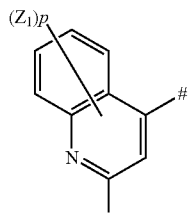

Chemical Formula 2-18
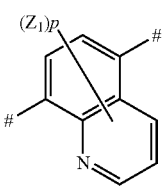

Chemical Formula 2-19
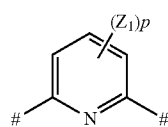

Chemical Formula 2-20
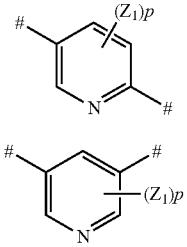

Chemical Formula 2-21
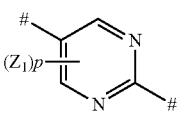

Chemical Formula 2-22
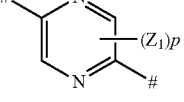

Chemical Formula 2-23
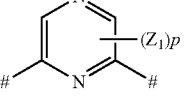

Chemical Formula 2-24 wherein $Z_1$ and $Z_2$ are each independently selected from the group consisting of a hydrogen atom, a substituted or unsubstituted C6 to C30 aryl, a substituted or unsubstituted C6 to C30 fused aryl, a substituted or unsubstituted C6 to C30 fused heteroaryl, a substituted or unsubstituted C1 to C16 alkyl, a substituted or unsubstituted C1 to C16 alkoxy;

p and q are each an integer independently selected from 0-6; and # indicates a position bonded with A or B.

According to an embodiment of the present disclosure, L is any one of the following groups:

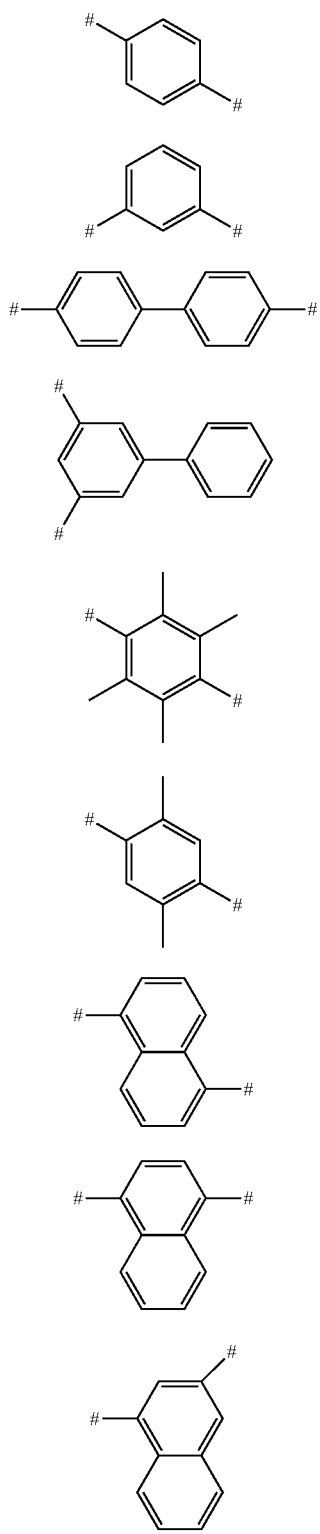

Chemical Formula 3-1

Chemical Formula 3-2

Chemical Formula 3-3

Chemical Formula 3-4

Chemical Formula 3-5

Chemical Formula 3-6

Chemical Formula 3-7

Chemical Formula 3-8

Chemical Formula 3-9

-continued

Chemical Formula 3-10

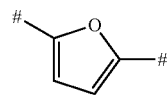

Chemical Formula 3-11

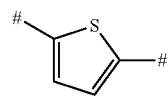

Chemical Formula 3-12

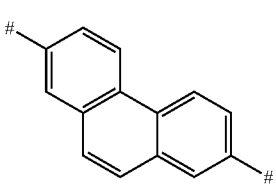

Chemical Formula 3-13

Chemical Formula 3-14

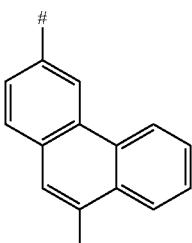

Chemical Formula 3-15

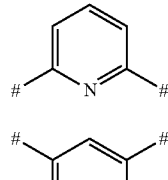

Chemical Formula 3-16

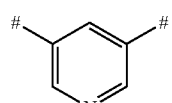

Chemical Formula 3-17

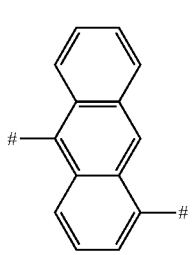

Chemical Formula 3-18

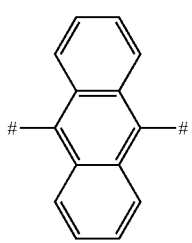

Chemical Formula 3-19

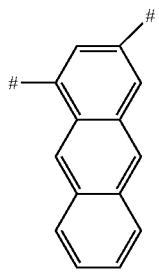

Chemical Formula 3-20

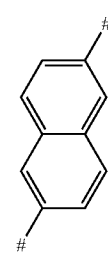

According to an embodiment of the present disclosure, $R_1$ to $R_8$ are each a hydrogen atom. In the present embodiment, when $R_1$-$R_8$ are each a hydrogen atom, a mother nucleus of the molecule of the electron transmission material is phenanthroline or pyridonaphthalene. Without wishing to be bound by the theory, it is believed this means it can improve the rigidity and regularity of the molecule, resulting in the amorphous film morphology of the electron transmission material, thereby improving the feasibility of evaporation.

According to an embodiment of the present disclosure, among $R_1$ to $R_8$, $R_3$ and $R_7$ are phenyl, and $R_1$, $R_2$, $R_4$-$R_6$, and $R_8$ are each a hydrogen atom.

According to an embodiment of the present disclosure, among $R_1$ to $R_8$, $R_7$ is phenyl, and $R_1$-$R_6$ and $R_8$ are each a hydrogen atom.

In the above two embodiments, $R_3$ and/or $R_7$ are phenyl, which leads to a certain twist of the plane of the molecule of the compound. Without wishing to be bound by theory, it is believed that such a twist increases the solubility of the compound. Phenyl is substituted at position of $R_3$ and/or $R_7$, so that the distortion of the molecular plane reduces the stack regularity of the molecule of the compound to some extent, and thus facilitates fabrication of the OLED device through evaporation. Further, a compound in which $R_3$ and/or $R_7$ are phenyl has a wide range of sources, i.e., the sources are available on the market and thus reducing synthesis costs of the compound.

According to an embodiment of the present disclosure, among $X_1$-$X_{10}$, $X_2$ and $X_{10}$ are each a nitrogen atom, and the rest are each a carbon atom. In this embodiment, when $X_2$ and $X_{10}$ are each a nitrogen atom, the formed pyridyl has a lone pair of electrons, which facilitates doping between the electron transmission material and the metal ion, thereby improving electron mobility and efficiency of device.

According to an embodiment of the present disclosure, $R_9$ and $R_{10}$ are each independently a hydrogen atom or pyridyl. In the case that both $R_9$ and $R_{10}$ are hydrogen atoms, there are many available raw materials for synthesis. In the case that both R9 and R10 are hydrogen atoms, the presence of the pyridyl further promotes doping between the electron transmission material and the metal, thereby further increasing the electron mobility and the efficiency of device.

According to an embodiment of the present disclosure, L is any one of the following groups:

Chemical Formula 3-1

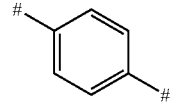

Chemical Formula 3-2

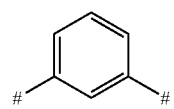

Chemical Formula 3-3

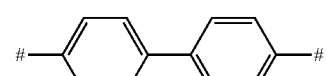

Chemical Formula 3-4

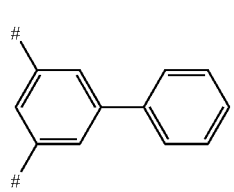

Chemical Formula 3-7

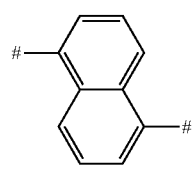

Chemical Formula 3-8

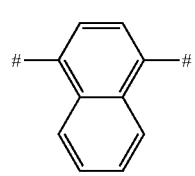

Chemical Formula 3-10

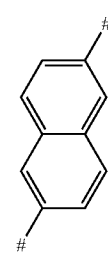

Chemical Formula 3-17

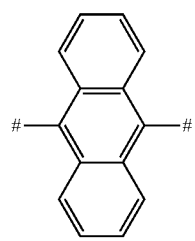

and B is selected from any of the following groups:
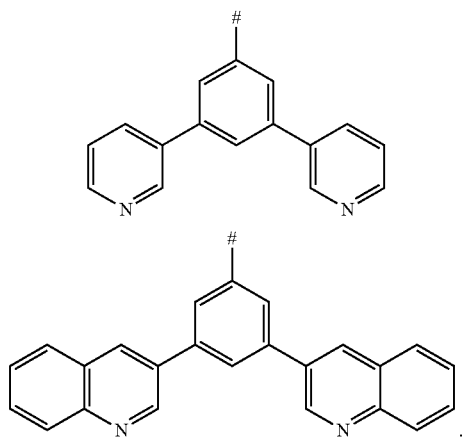
According to an embodiment of the present disclosure, the compound is any one of the following compounds:
ET001
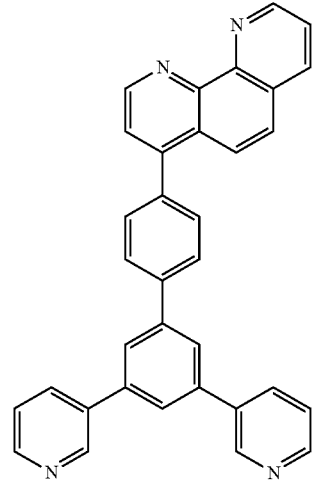
ET002
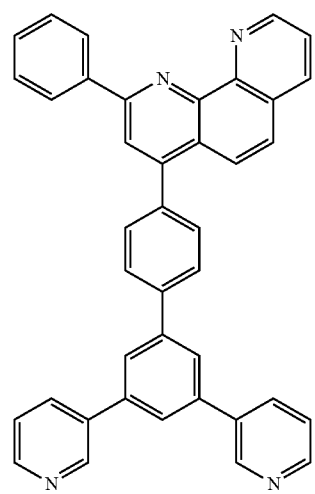
ET003
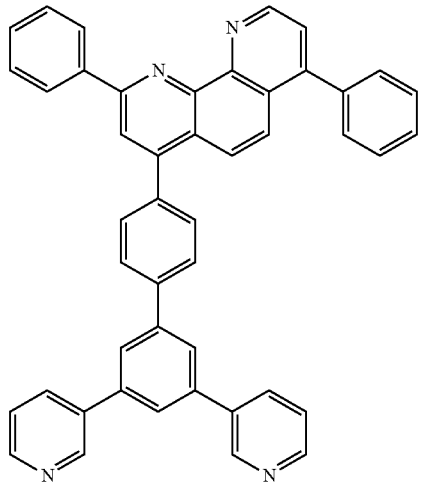
ET004
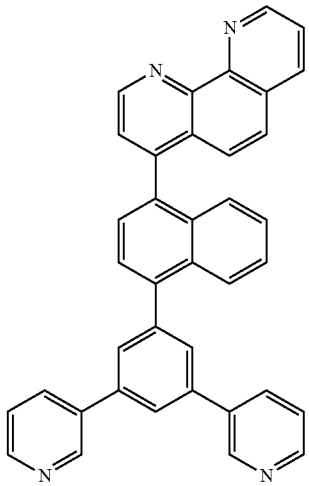
ET005
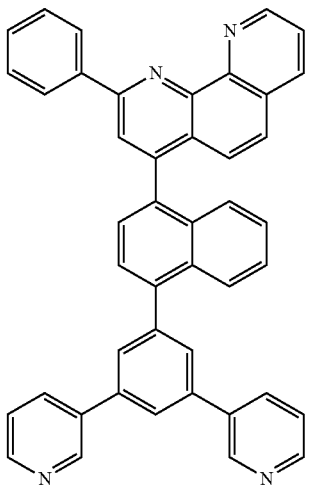

-continued
ET006
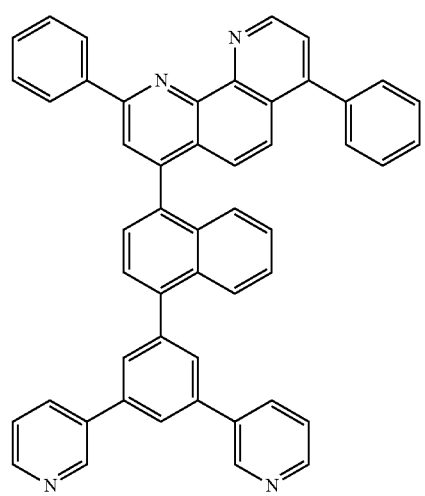
ET007
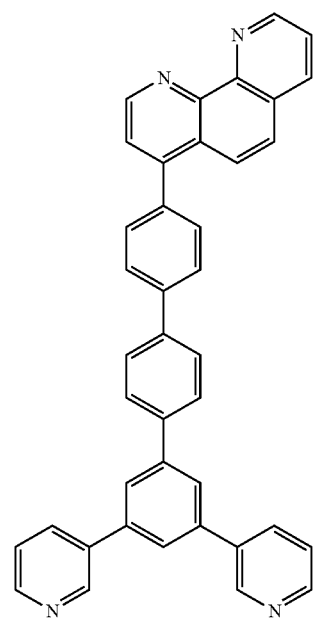
ET008
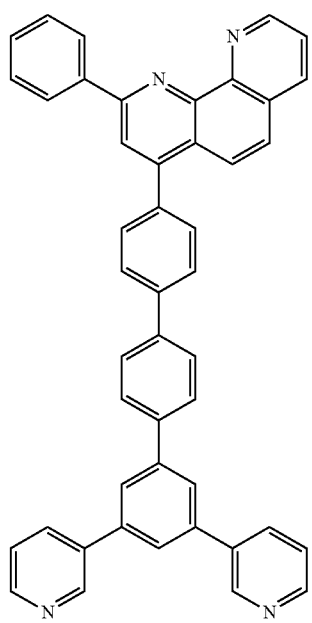
ET009
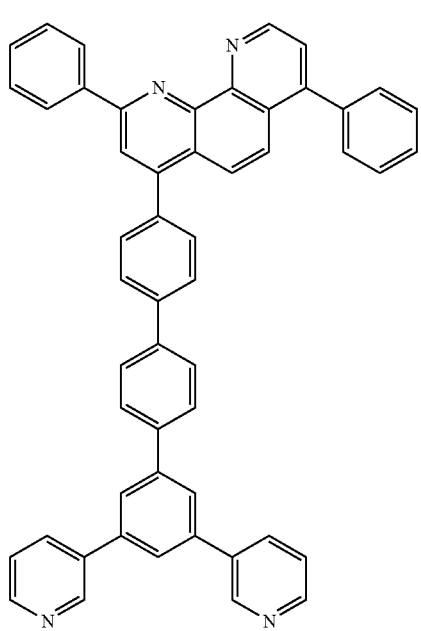

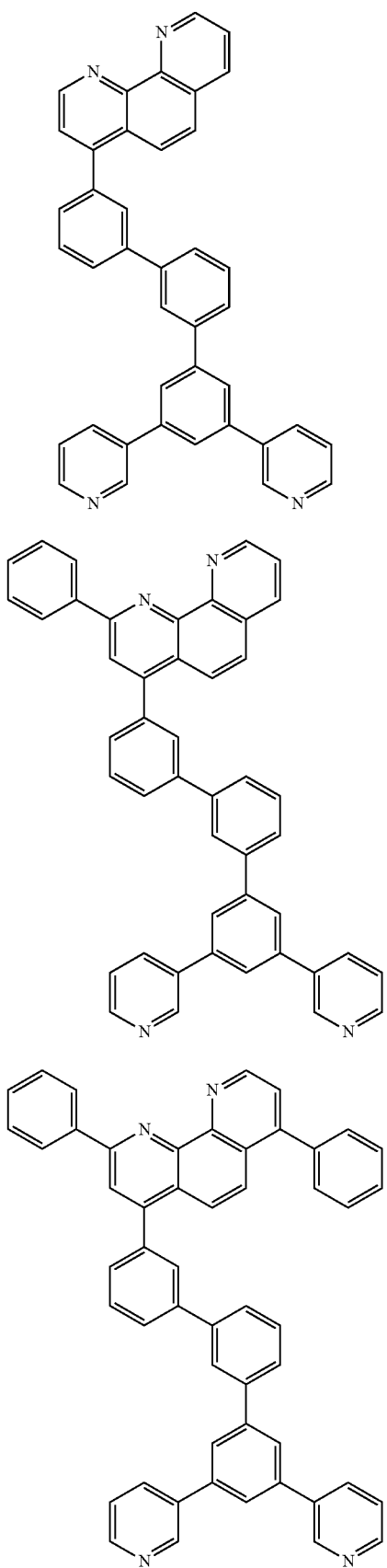
ET010
ET011
ET012
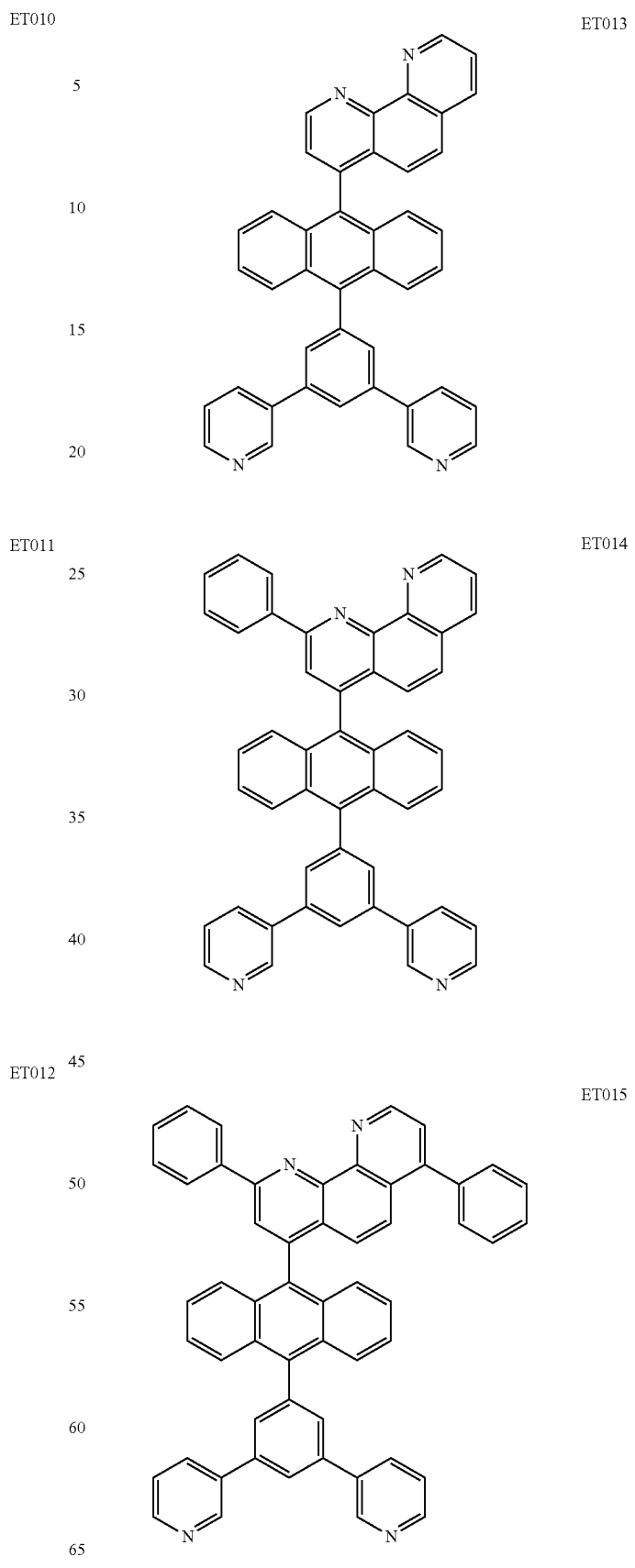
ET013
ET014
ET015

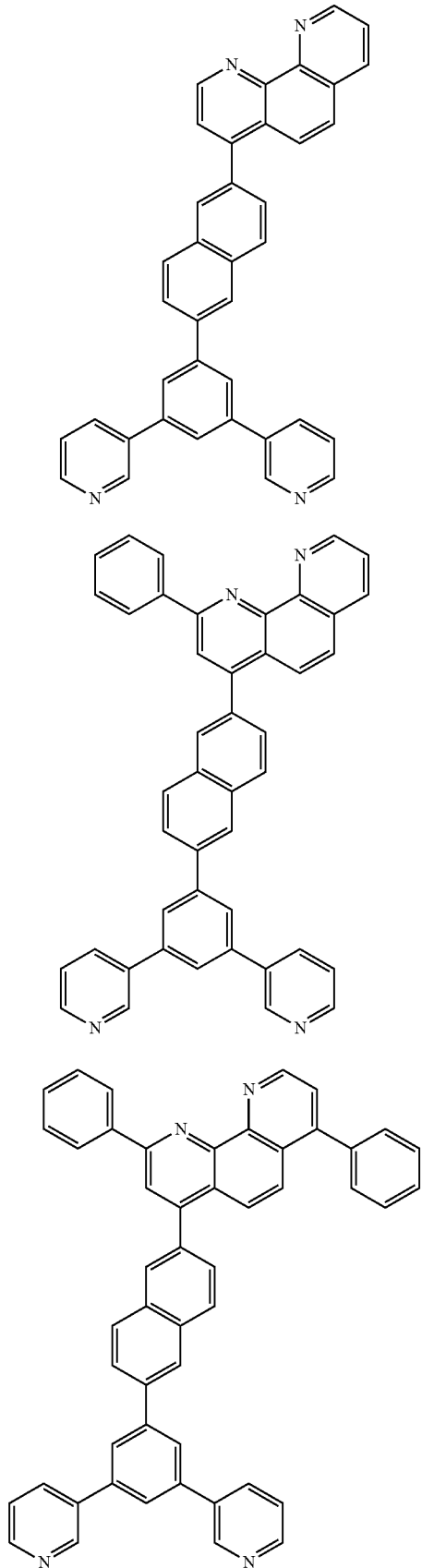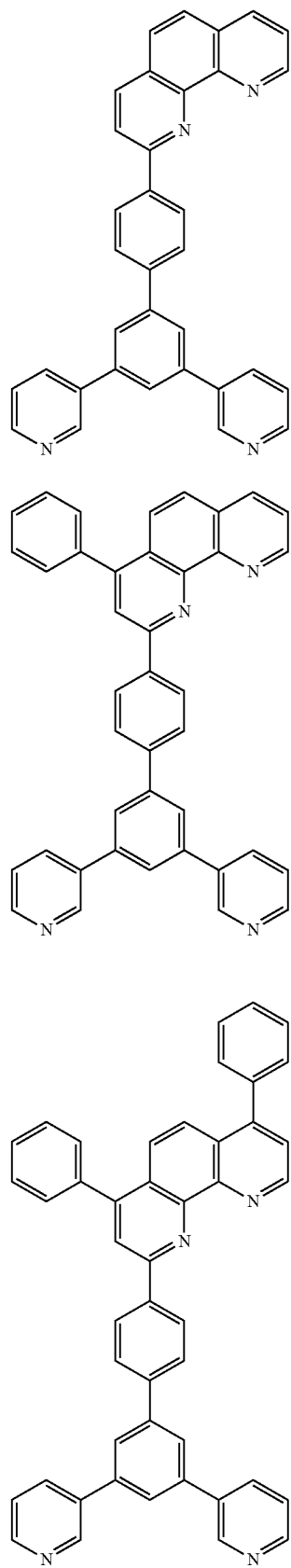

ET022
ET023
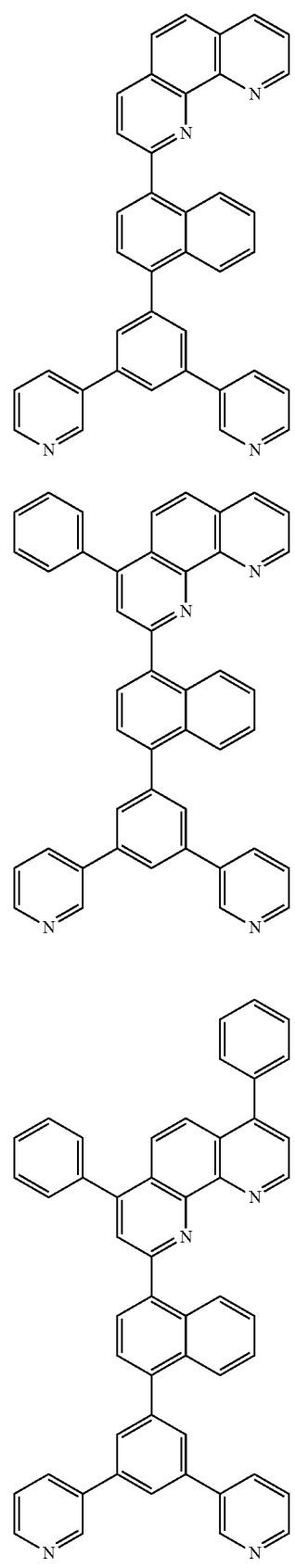
ET025
ET026
ET024

ET027
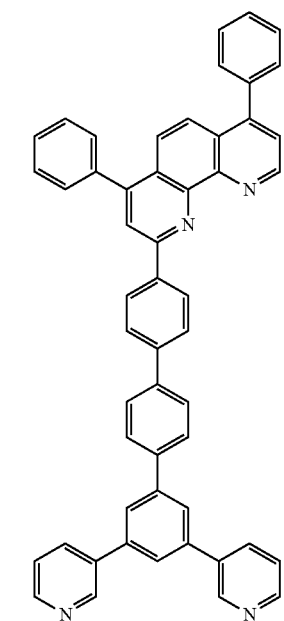
ET028
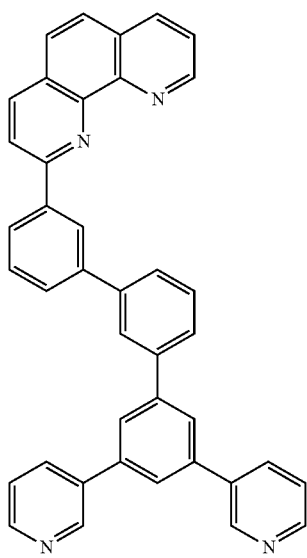
ET029
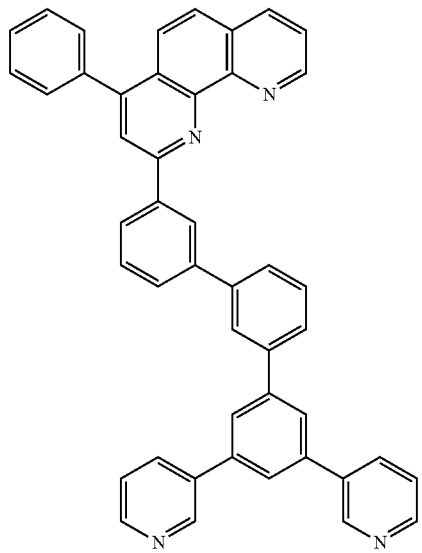
ET030
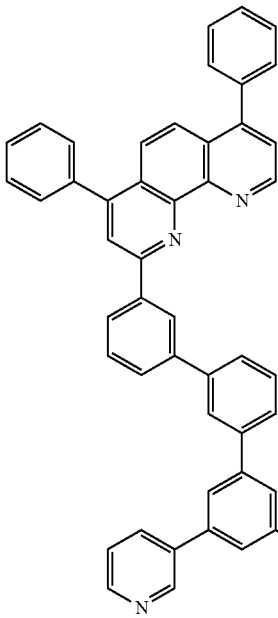
ET031
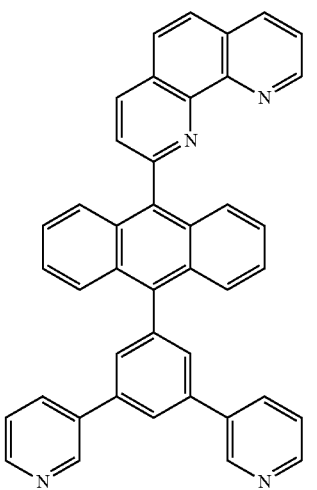

-continued
ET032
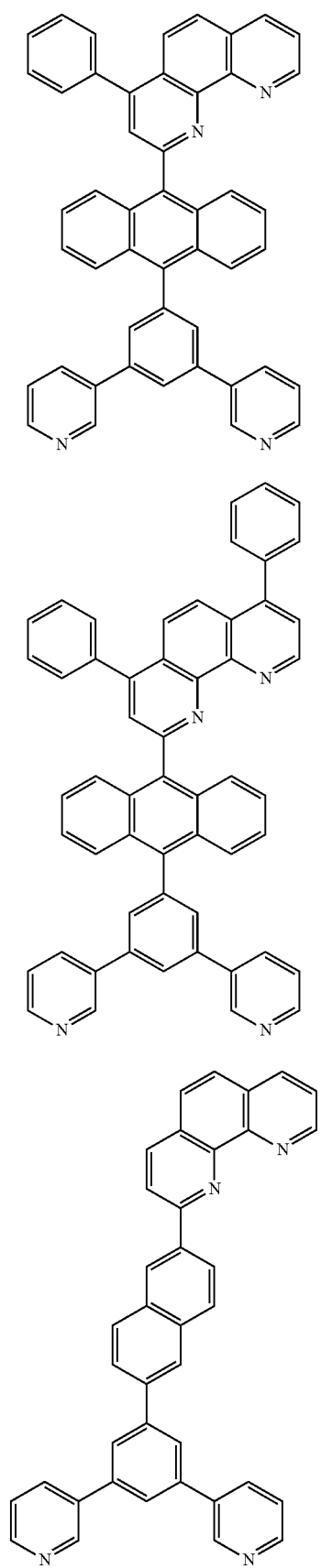
ET033
ET034
-continued
ET035
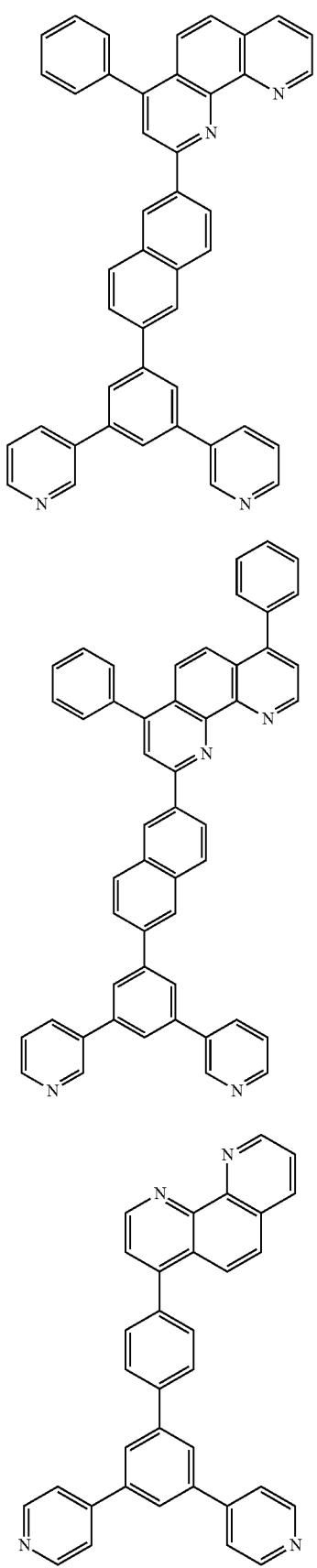
ET036
ET037

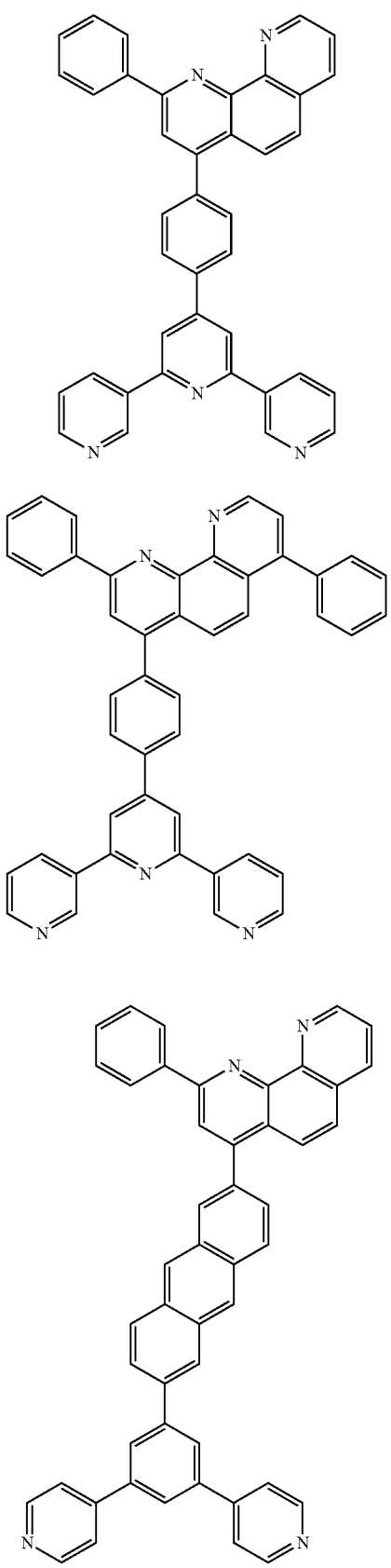
ET038
ET039
ET040
ET041
ET042

ET043
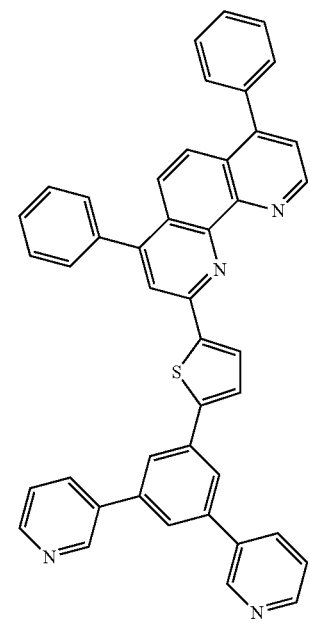
ET044
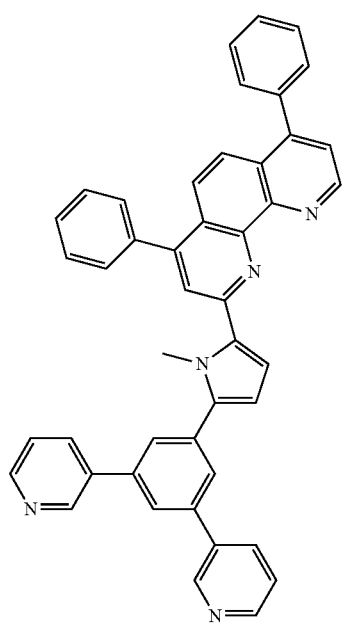
ET045
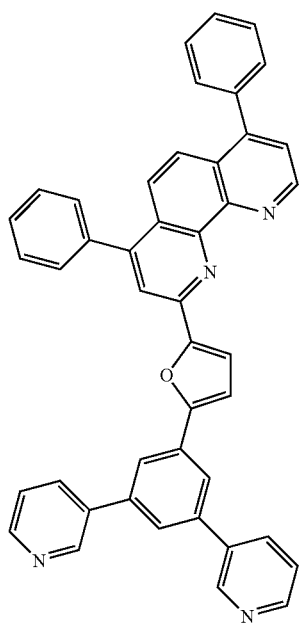
ET046
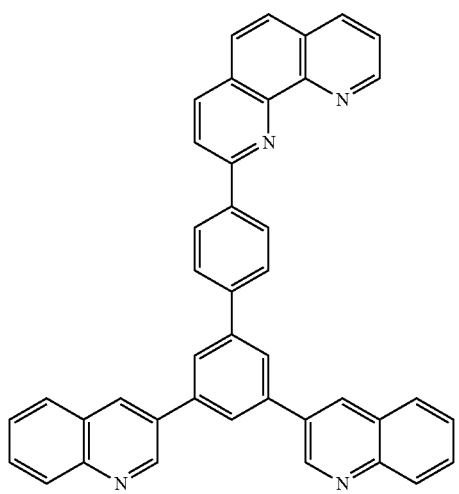
ET047
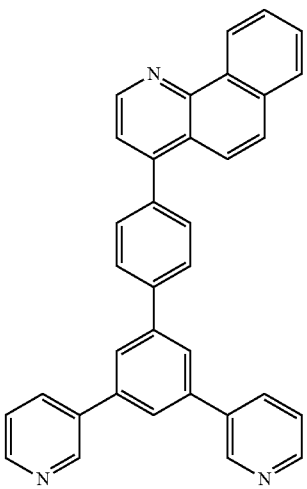

ET048
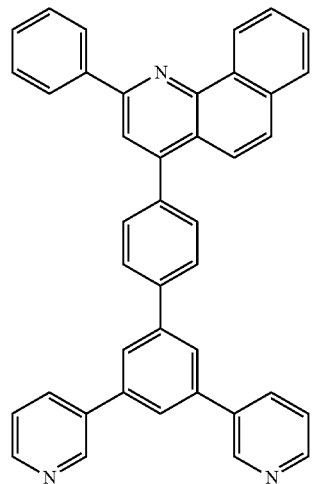
ET049
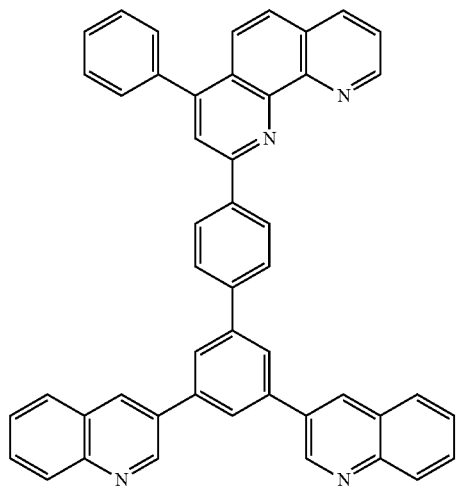
ET050
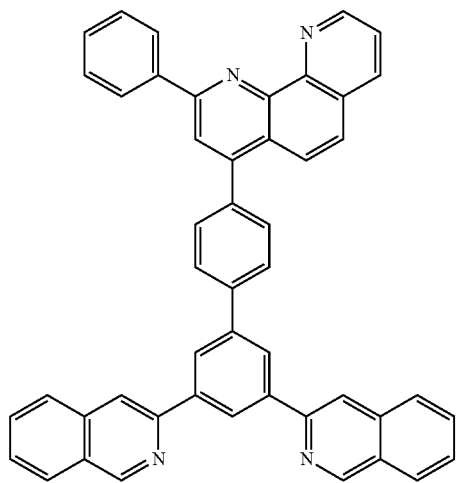
ET051
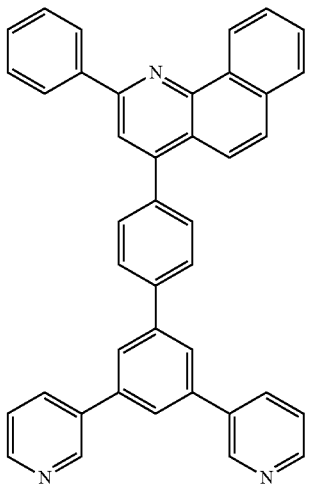
ET052
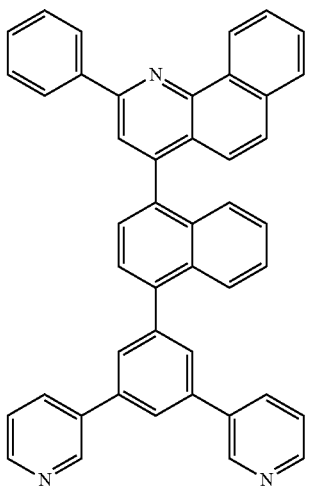
ET053
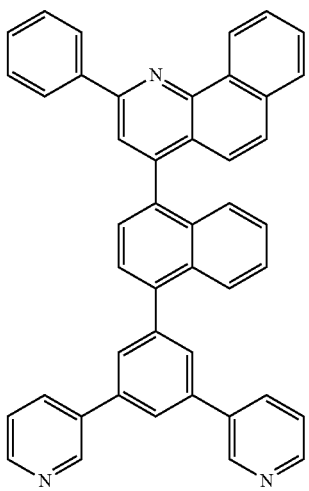

-continued
ET054
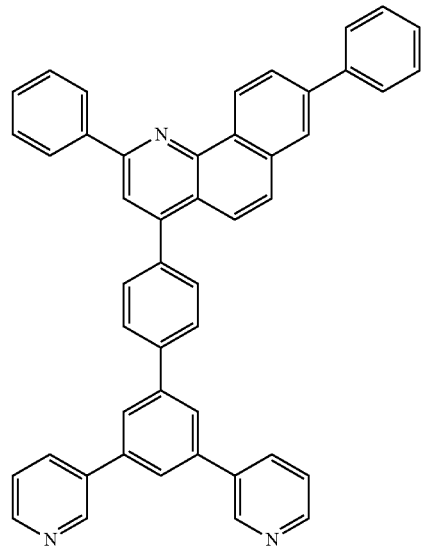
-continued
ET056
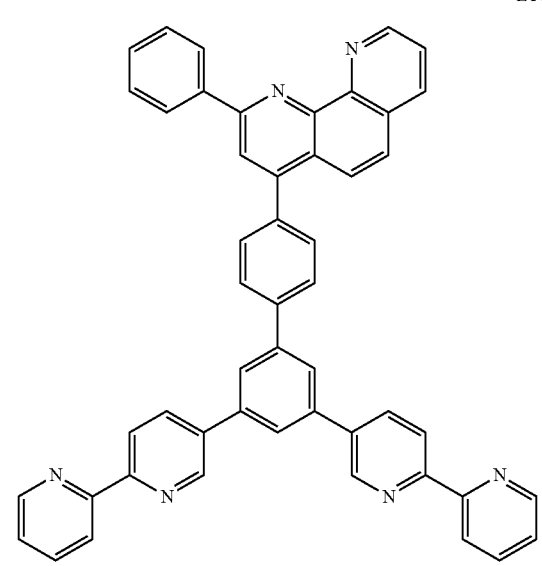
ET055
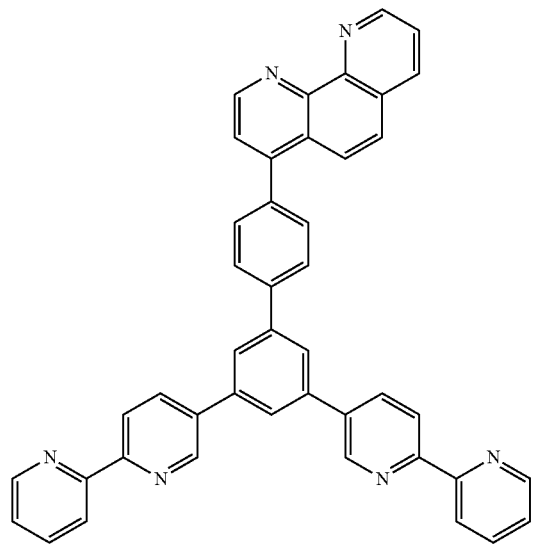
ET055
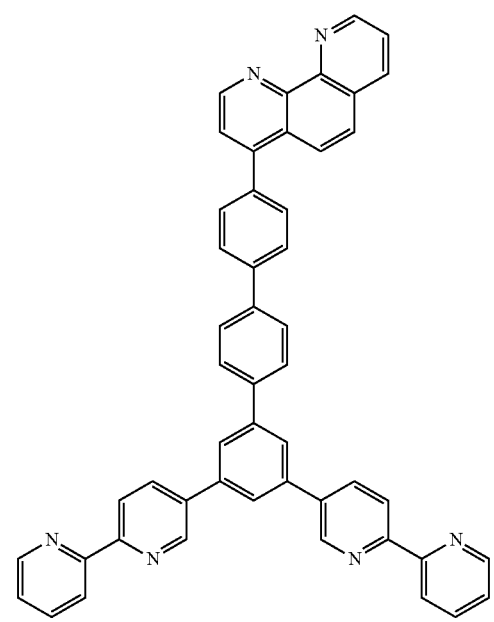

ET056

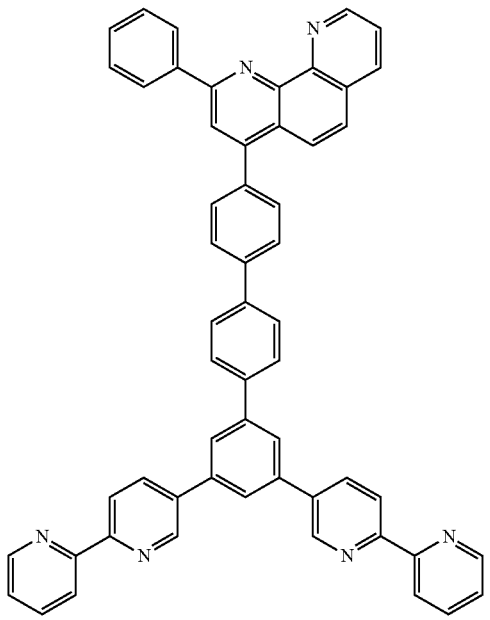

ET057

ET058

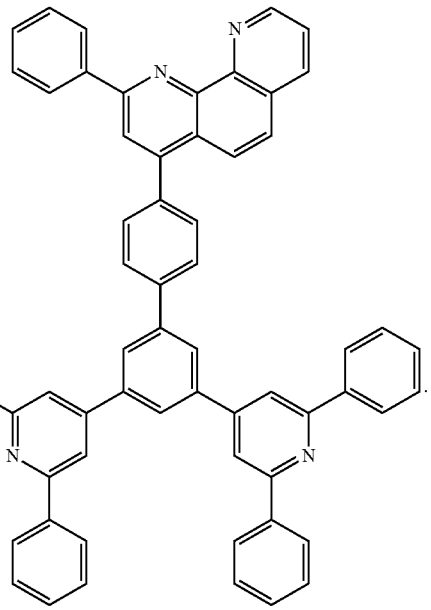

According to the compound of the present disclosure, the compound has a glass transition temperature of greater than or equal to 120° C.

In an embodiment, the compounds of the present disclosure are suitable for use as electron transmission materials for OLEDs. FIG. 1 shows a chemical structure of an exemplary Compound ET003 according to an embodiment of the present disclosure.

Accordingly, the present disclosure also provides a display panel including an organic light-emitting device. The organic light-emitting device includes an anode, a cathode opposite to the anode, and an electron transmission layer and a light-emitting layer that are disposed between the anode and the cathode. The material of the electron transmission layer includes one or more of the compounds according to the present disclosure.

In an embodiment, the display panel further includes an electron injection layer, wherein an energy level difference between a LUMO energy level value of a material of the electron transmission layer and a LUMO energy level value of a material of the light-emitting layer or the electron injection layer is smaller than 0.2 eV; and a HOMO energy level of the material of the electron transmission layer is at least 0.3 eV higher than a HOMO level value of the material of the electron injection layer. By defining the energy difference between the LUMO energy levels of the respective materials, the electron transmission efficiency of the light-emitting device in the display panel can be ensured, thereby ensuring the light-emitting efficiency of the light-emitting device.

In an embodiment, the electron injection layer includes the compound of a present disclosure and a doped metal. According to an embodiment, the doped metal is selected from the group consisting of sodium, potassium, calcium, cesium, ytterbium, and combinations thereof. The doped metal can avoid the excessively high interface energy barrier between the electron transmission layer and the cathode in the existing organic light-emitting display panel, and thus solve the problem of low performance of the organic light-emitting display panel. By doping the metal in the electron injection layer, the interface energy barrier between the electron transmission layer and the cathode of the organic light-emitting display panel is increased, the electron injecting capability is improved, and the performance of the organic light-emitting display panel is improved.

According to the display panel of the present disclosure, the content of the doped metal in the electron injection layer can be 1 wt % to 5 wt %. In an embodiment, the content of the doped metal in the electron injection layer is 3 wt %. Without wishing to be bound by theory, it is believed that when the content of the doped metal in the electron injection layer is too low, the nitrogen atom in the phenanthroline and the outer electrons of the metal element cannot effectively form an electron cloud and a large π C bond, the ability of electron injection and transmission cannot be effectively improved, and the corresponding electron transmission effect cannot be achieved. If the content of the doped metal in the electron injection layer is too high, an exciton quenching phenomenon can occur in the light-emitting layer. The exciton quenching phenomenon indicates that an interface in contact with the light-emitting layer contains excessive metal, the excitons generated in the light-emitting layer are easily affected by the metal at the interface, thereby causing energy quenching, leading to a poor efficiency of device, and greatly reducing the OLED light-emitting efficiency.

In an embodiment, the organic light-emitting device further includes one or more layers of a hole injection layer, a hole transmission layer, an electron blocking layer, a hole blocking layer, or an electron injection layer.

The light-emitting property of various devices requires a suitable match among the light-emitting functional layers. Therefore, different organic light-emitting functional layers can be selected according to different display requirements and selected compounds.

Another aspect of the present disclosure describes several synthesis of the exemplary organic compounds ET002, ET026, ET035 and ET048.

Synthesis of Intermediate
2-phenyl-4-chloro-1,10-phenanthroline

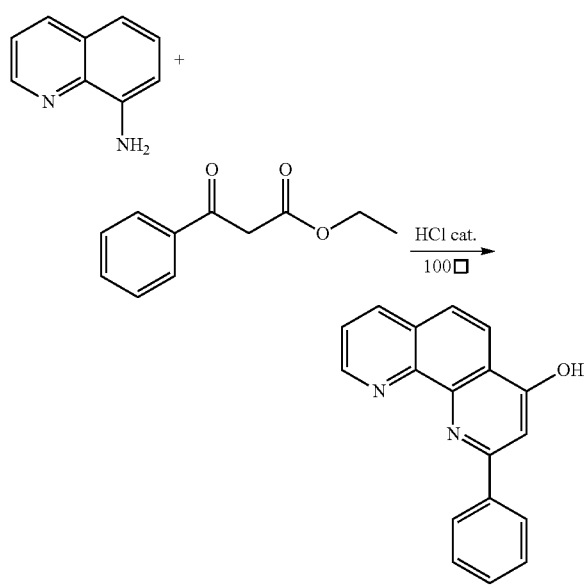

A mixture of 8-aminoquinoline (50 mmol) and ethyl acetoacetate (50 mmol) was stirred at 100° C. for 24 h, and as catalyst, about 10 drops of HCl were added. The reaction mixture was cooled at room temperature, 20 mL of toluene was added and then removed by rotary distillation under reduced pressure. The same process was repeated three times. The formed brown oily crude enamine was dissolved in 20 mL of diphenyl ether, and 70 mL of the enamine solution was slowly added to the diphenyl ether at 260° C. for 15 minutes. After 30 minutes, the reaction mixture was cooled to room temperature and hexane was poured thereto. The solvent was then decanted, and the residue was crystallized in dichloromethane and ethyl acetate to obtain a pale brown solid 2-phenyl-4-hydroxy-1,10-phenanthroline.

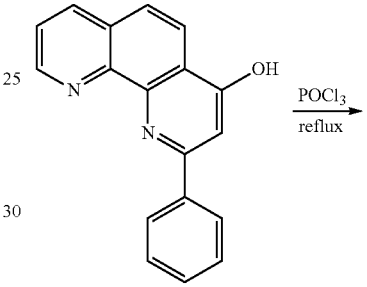

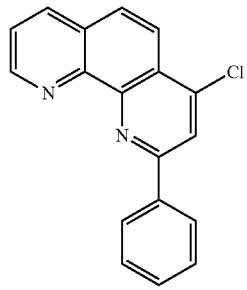

2-phenyl-4-hydroxy-1,10-phenanthroline (25 mol) was slowly added to phosphorus oxychloride (60 mL) and mixed for another 4 h. The reaction mixture was cooled to room temperature and the solvent was removed under reduced pressure. The mixture was treated with dichloromethane and saturated NaHCO₃ to obtain solid, and then the organic phase was separated. The aqueous layer was further extracted with dichloromethane. The collected organic phase was washed by saline, dried with MgSO₄, and then filtered and concentrated. The residue was recrystallized in dichloromethane and ethyl acetate to obtain pale brown solid 2-phenyl-4-chloro-1,10-phenanthroline.

Example 1

Synthesis of Compound ET002

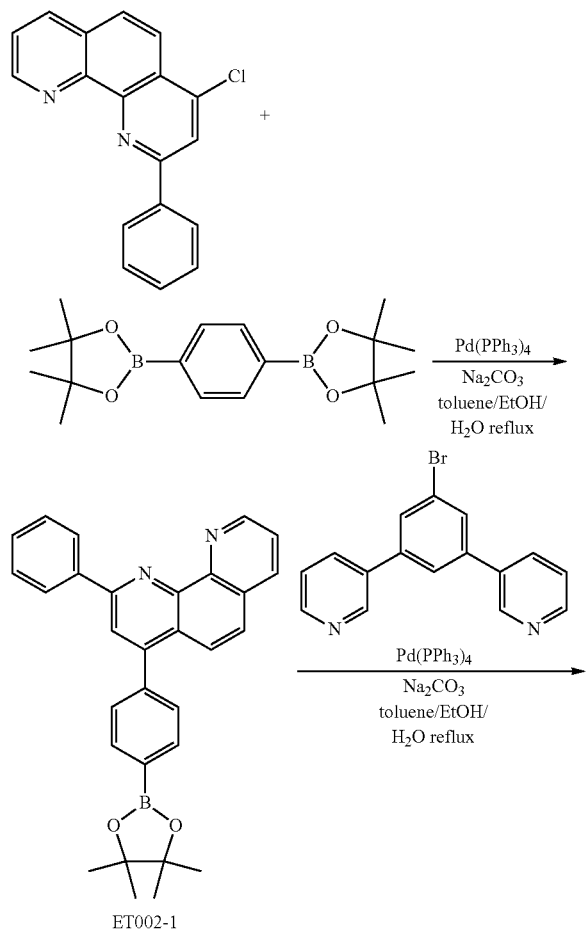

2-phenyl-4-chloro-1,10-phenanthroline (10 mmol), 1,4-diborate-benzene (10 mmol) and $Na_2CO_3$ (80 mmol) were added to a solvent of toluene/EtOH (anhydrous ethanol)/$H_2O$ (75/25/50, mL) so as to form a mixed solution. Then, $Pd(PPh_3)_4$ (0.48 mmol) was added to the above mixed solution, and the mixture was refluxed for 20 h under nitrogen atmosphere. The obtained mixture was then cooled to room temperature and extracted with ethyl acetate. The aqueous layer was further extracted with dichloromethane. The collected organic phase was washed with brine, then dried with $MgSO_4$, filtered and concentrated. The residue was recrystallized in dichloromethane and methanol to obtain intermediate ET002-1.

The intermediate ET002-1 (10 mmol) obtained in the previous step, 1-bromo-3,5-dipyridyl-benzene (10 mmol) and $Na_2CO_3$ (80 mmol) were respectively added to a solvent of toluene/EtOH (anhydrous ethanol)/$H_2O$ (75/25/50, mL) so as to form a mixed solution. Then $Pd(PPh_3)_4$ (0.48 mmol) was added to the above mixed solution, and the mixture was refluxed for 20 h under nitrogen atmosphere. The obtained mixture was then cooled to room temperature and extracted with ethyl acetate. The aqueous layer was further extracted with dichloromethane. The collected organic phase was washed with brine, then dried with $MgSO_4$, filtered and concentrated. The residue was recrystallized in dichloromethane and methanol to obtain product ET002.

Elemental analysis of the Compound ET002 (Molecular Formula $C_{40}H_{26}N_4$): theoretical values: C, 85.38; H, 4.66; N, 9.96. Found: C, 85.38; H, 4.67; N, 9.95. ESI-MS (m/z) (M+) was obtained by liquid chromatograph mass spectrometry: theoretical values: 562.22, found: 562.66.

Example 2

Synthesis of Compound ET026

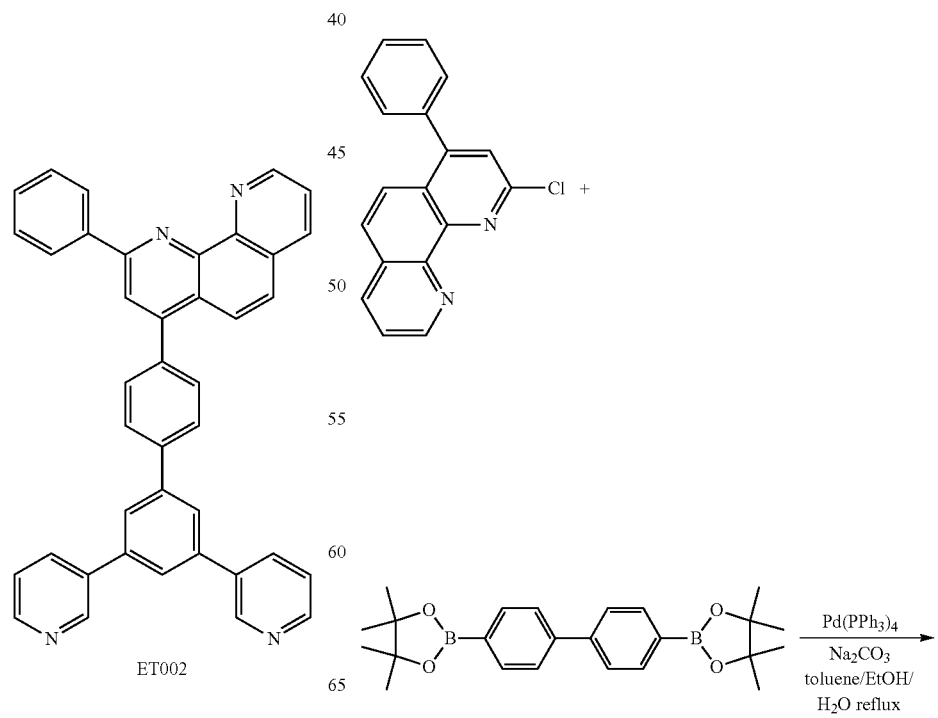

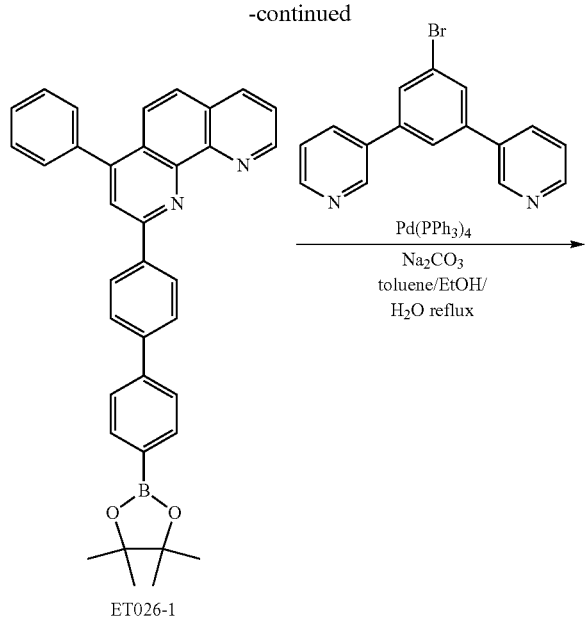

4-phenyl-2-chloro-1,10-phenanthroline (10 mmol), 1,6-diphenyl diborate (10 mmol) and Na$_2$CO$_3$ (80 mmol) were added to a solvent of toluene/EtOH (anhydrous ethanol)/H$_2$O (75/25/50, mL) so as to form a mixed solution. Then, Pd(PPh$_3$)$_4$ (0.48 mmol) was added to the above mixed solution, and the mixture was refluxed 20 h under nitrogen atmosphere. The obtained mixture was then cooled to room temperature and extracted with ethyl acetate. The aqueous layer was further extracted with dichloromethane. The collected organic phase was washed with brine, then dried with MgSO$_4$, filtered and concentrated. The residue was recrystallized in dichloromethane and methanol to obtain intermediate ET026-1.

The intermediate ET026-1 (10 mmol) obtained in the previous step, 1-bromo-3,5-dipyridyl-benzene (10 mmol) and Na$_2$CO$_3$ (80 mmol) were respectively added to a solvent of toluene/EtOH (anhydrous ethanol)/H$_2$O (75/25/50, mL) so as to form a mixed solution. Then Pd(PPh$_3$)$_4$ (0.48 mmol) was added to the above mixed solution, and the mixture was refluxed for 20 h under nitrogen atmosphere. The obtained mixture was then cooled to room temperature and extracted with ethyl acetate. The aqueous layer was further extracted with dichloromethane. The collected organic phase was washed with brine, then dried with MgSO$_4$, filtered and concentrated. The residue was recrystallized from dichloromethane and methanol to obtain product ET026.

Elemental analysis of the Compound ET026 (Molecular Formula C$_{46}$H$_{30}$N$_4$): theoretical values: C, 86.49; H, 4.73; N, 8.77. found: C, 86.49; H, 4.72; N, 8.78. ESI-MS (m/z) (M+) was obtained by liquid chromatograph mass spectrometry: theoretical values: 638.25, found: 638.76.

Example 3

Synthesis of Compound ET035

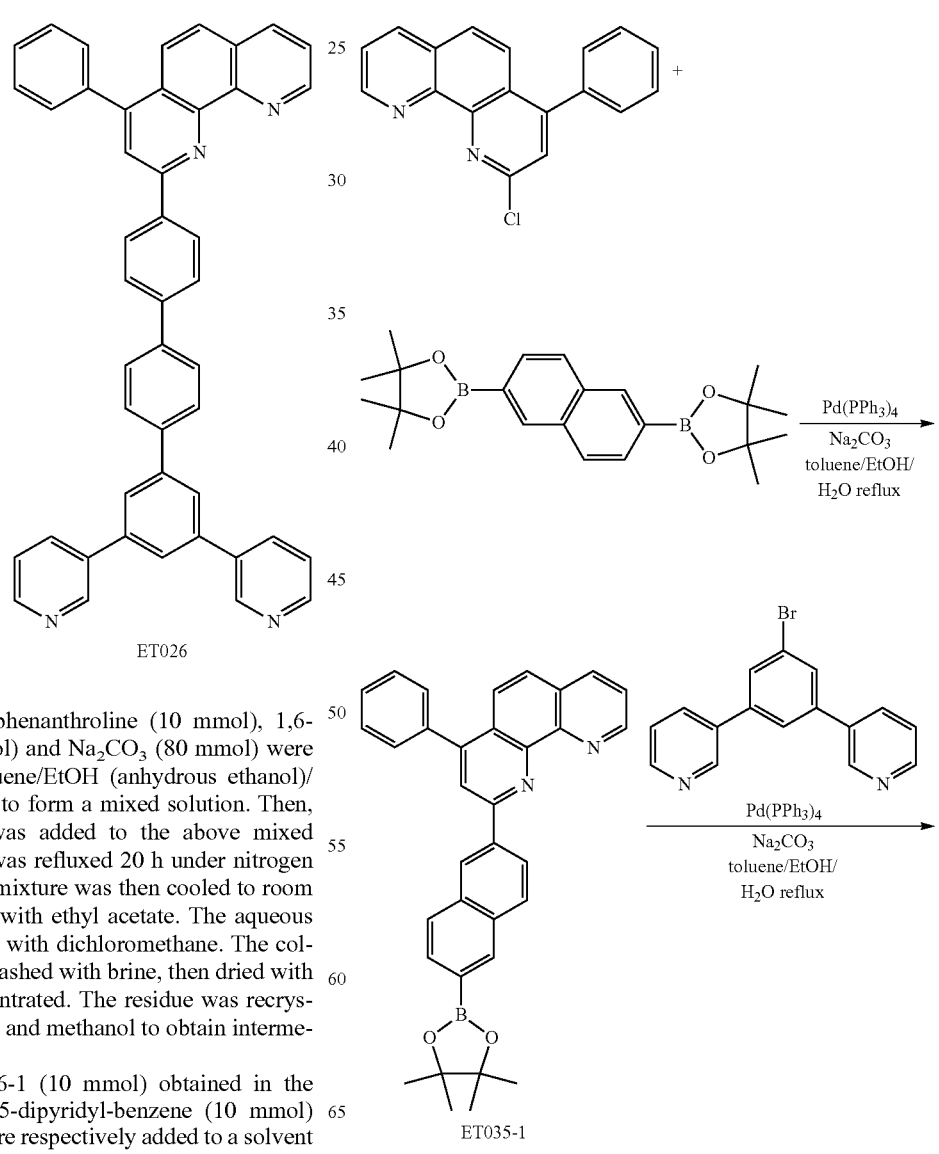

43
-continued

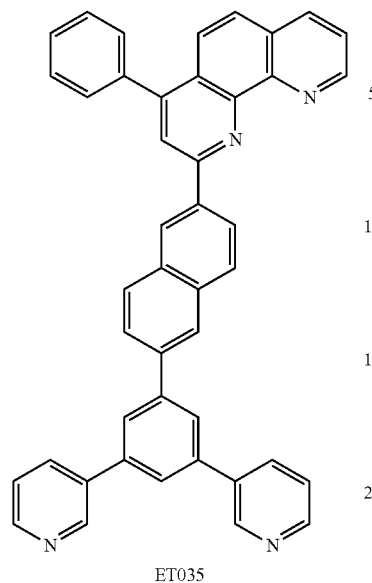

ET035

4-phenyl-1,10-phenanthroline-2-chloro (10 mmol), 2,6-diborate-naphthalene (10 mmol) and Na$_2$CO$_3$ (80 mmol) were added to a solvent of toluene/EtOH (anhydrous ethanol)/H$_2$O (75/25/50, mL) so as to form a mixed solution. Then, Pd(PPh$_3$)$_4$ (0.48 mmol) was added to the above mixed solution, and the mixture was refluxed for 20 h under nitrogen atmosphere. The obtained mixture was then cooled to room temperature and extracted with ethyl acetate. The aqueous layer was further extracted with dichloromethane. The collected organic phase was washed with brine, then dried with MgSO$_4$, filtered and concentrated. The residue was recrystallized in dichloromethane and methanol to obtain intermediate ET035-1.

The Intermediate ET035-1 (10 mmol) obtained in the previous step, 1-bromo-3,5-dipyridyl-benzene (10 mmol) and Na$_2$CO$_3$ (80 mmol) were respectively added to a solvent of toluene/EtOH (anhydrous ethanol)/H$_2$O (75/25/50, mL) so as to form a mixed solution. Then Pd(PPh$_3$)$_4$ (0.48 mmol) was added to the above mixed solution, and the mixture was refluxed for 20 h under nitrogen atmosphere. The obtained mixture was then cooled to room temperature and extracted with ethyl acetate. The aqueous layer was further extracted with dichloromethane. The collected organic phase was washed with brine, then dried with MgSO$_4$, filtered and concentrated. The residue was recrystallized in dichloromethane and methanol to obtain product ET035.

44

Example 4

Synthesis of Compound ET048

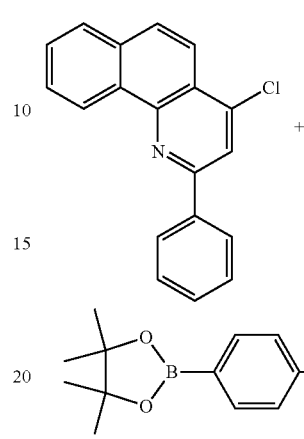

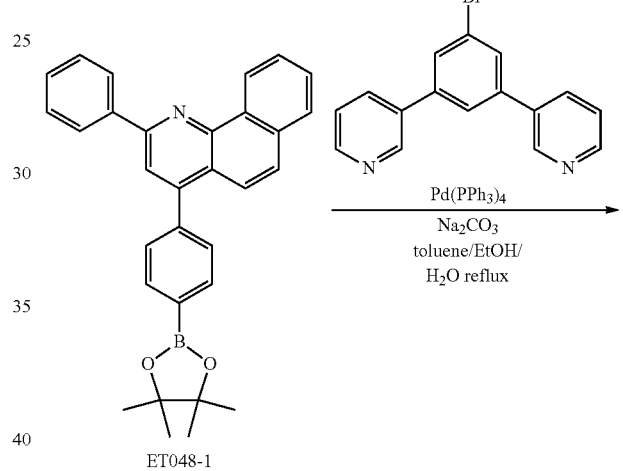

ET048-1

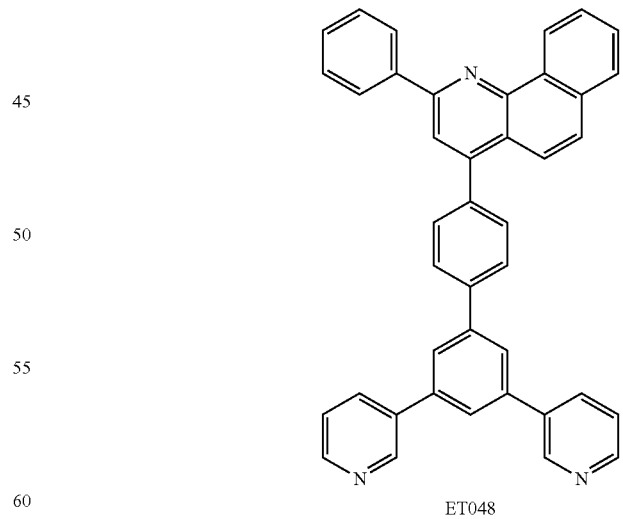

ET048

2-phenyl-benzo[H]quinoline-4-chloro (10 mmol), 1,4-diborate-benzene (10 mmol) and Na$_2$CO$_3$ (80 mmol) were added to a solvent of toluene/EtOH (anhydrous ethanol)/H$_2$O (75/25/50, mL) so as to form a mixed solution. Then, Pd(PPh$_3$)$_4$ (0.48 mmol) was added to the above mixed solution, and the mixture was refluxed for 20 h under nitrogen atmosphere. The obtained mixture was then cooled to room temperature and extracted with ethyl acetate. The aqueous layer was further extracted with dichloromethane. The collected organic phase was washed with brine, then dried with MgSO$_4$, filtered and concentrated. The residue was recrystallized in dichloromethane and methanol to obtain intermediate ET048-1.

The intermediate ET048-1 (10 mmol) obtained in the previous step, 1-bromo-3,5-dipyridyl-benzene (10 mmol) and Na$_2$CO$_3$ (80 mmol) were respectively added to a solvent of toluene/EtOH (anhydrous ethanol)/H$_2$O (75/25/50, mL) so as to form a mixed solution. Then Pd(PPh$_3$)$_4$ (0.48 mmol) was added to the above mixed solution, and the mixture was refluxed for 20 h under nitrogen atmosphere. The obtained mixture was then cooled to room temperature and extracted with ethyl acetate. The aqueous layer was further extracted with dichloromethane. The collected organic phase was washed with brine, then dried with MgSO$_4$, filtered and concentrated. The residue was recrystallized in dichloromethane and methanol to obtain product ET048.

Elemental analysis of the Compound ET048 (Molecular Formula C$_{41}$H$_{27}$N$_3$): theoretical values: C, 87.67; H, 4.85; N, 7.48. found: C, 87.67; H, 4.86; N, 7.47. ESI-MS (m/z) (M+) was obtained by liquid chromatograph mass spectrometry: theoretical values: 561.22, found: 561.67.

Device Example 1

Figure 2:
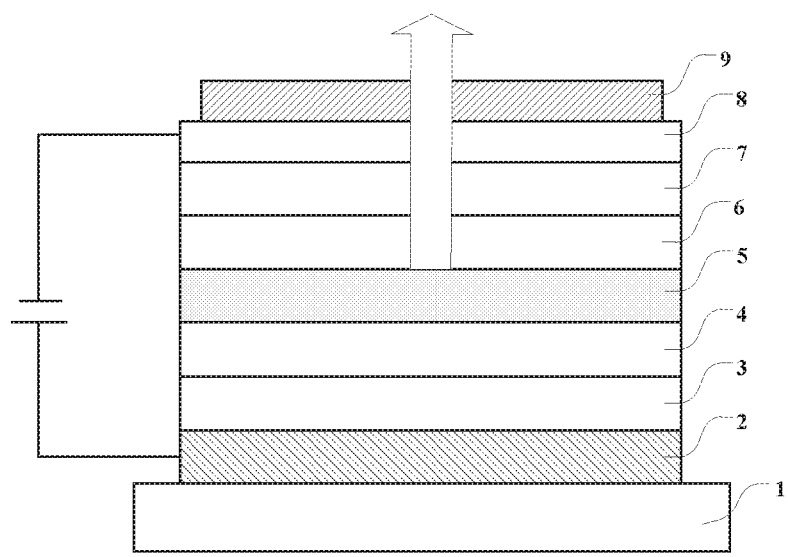
FIG. 2 is a structural schematic diagram of an organic light-emitting diode (OLED) device according to an embodiment of the present disclosure.

This example provides an organic light-emitting device. As shown in FIG. 2, the organic light-emitting device includes: a substrate 1, an ITO anode 2, a first hole transmission layer 3, a second hole transmission layer 4, a light-emitting layer 5, a first electron transmission Layer 6, a second electron transmission layer 7, a cathode 8 (magnesium silver electrode, a mass ratio of magnesium to silver is 9:1) and a capping layer CPL 9. The ITO anode 2 has a thickness of 15 nm. The first hole transmission layer 3 has a thickness of 10 nm. The second hole transmission layer 4 has a thickness of 95 nm. The light-emitting layer 5 has a thickness of 30 nm. The first electron transmission layer 6 has a thickness of 30 nm. The second electron transmission layer 7 has a thickness of 5 nm. The magnesium silver electrode 8 has a thickness of 15 nm. The capping layer CPL 9 has a thickness of 100 nm.

The steps for preparing the organic light-emitting device according to the present disclosure are as follows.

1) A glass substrate 1 was cut into a size of 50 mm×50 mm×0.7 mm, subjected to ultrasonic treatments in isopropyl alcohol and in deionized water for 30 minutes, respectively, and then exposed to ozone for about 10 minutes for cleaning. The obtained glass substrate with an ITO anode 2 was mounted on a vacuum deposition apparatus.

2) A hole injection layer material HAT-CN was evaporated on the ITO anode 2 by vacuum evaporation to obtain a layer having a thickness of 10 nm and used as the first hole transmission layer 3.

3) The material TAPC of the second hole transmission layer 4 was evaporated by vacuum evaporation on the first hole transmission layer 3 to obtain a layer having a thickness of 95 nm and used as the second hole transmission layer 4.

4) The light-emitting layer 5 was co-deposited on the hole transmission layer 4, where DPVBi was used as a host material, BCzVBi is used as a doping material, and a mass ratio of DPVBi to BCzVBi was 1:19. The light-emitting layer 5 has a thickness of 30 nm.

5) The material ET002 of the first electron transmission layer 6 was evaporated on the light-emitting layer 5 so as to obtain the first electron transmission layer 6 having a thickness of 30 nm.

6) The material Alq3 of the second electron transmission layer 7 was evaporated by vacuum evaporation on the first electron transmission layer 6 to obtain the second electron transmission layer 7 having a thickness of 5 nm.

7) Magnesium silver electrode was evaporated by vacuum evaporation on the second electron transmission layer 7 to manufacture the cathode 8 having a thickness of 15 nm, in which a mass ratio of Mg to Ag was 9:1.

8) The hole material CBP having a high refractive index was evaporated by vacuum evaporation on the cathode 8 to a thickness of 100 nm and used as a cathode covering layer (capping layer or CPL).

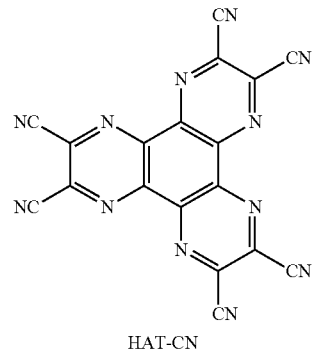

HAT-CN

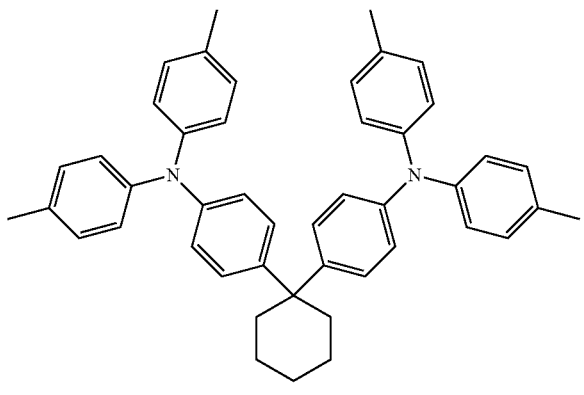

TAPC

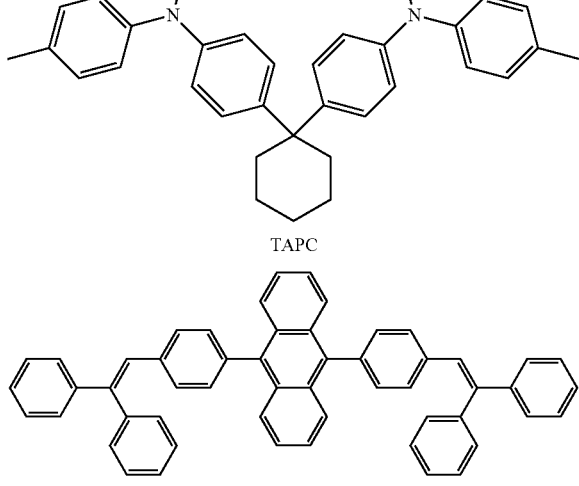

DPVBi

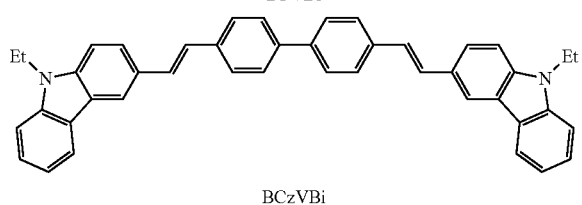

BCzVBi

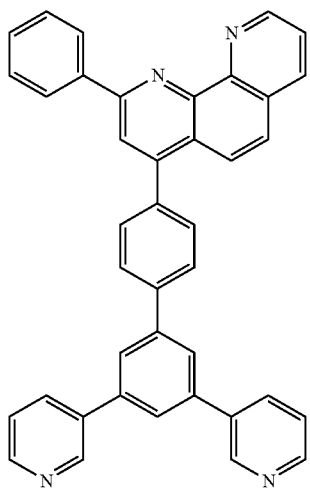

ET002

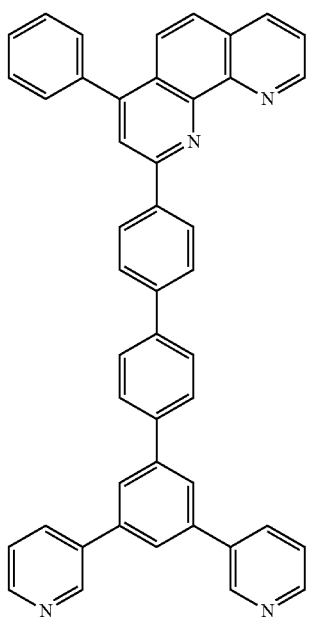

ET026

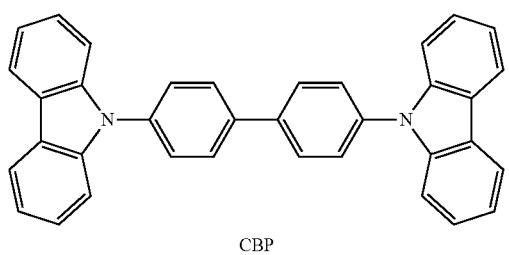

Alq3

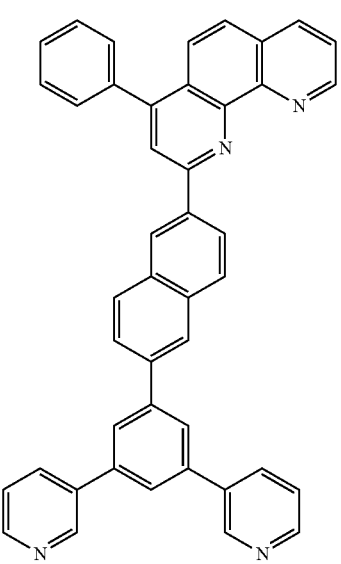

ET035

CBP

Device Example 2

Device Example 2 differs from Device Example 1 in that Compound ET026 is used as the first electron transmission layer 6. The other materials of other layers are all the same.

Device Example 3

Device Example 3 differs from Device Example 1 in that Compound ET035 is used as the first electron transmission layer 6. The other materials of other layers are all the same.

Device Example 4

Device Example 4 differs from Device Example 1 in that Compound ET048 is used as the first electron transmission layer 6. The other materials of other layers are all the same.

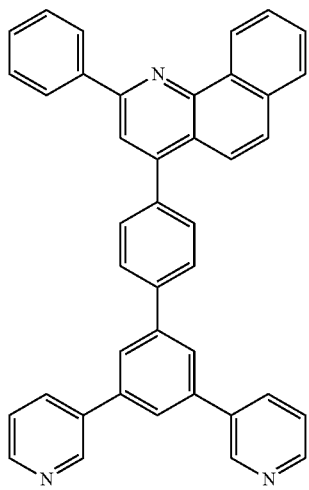

Device Comparative Example 1

Device Comparative Example 1 differs from Device Example 1 in that Compound BPhen is used as the first electron transmission layer 6. The other materials of other layers are all the same.

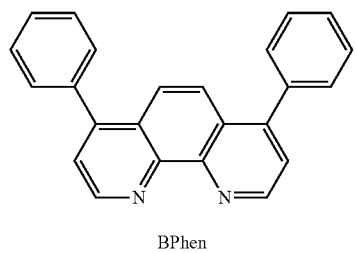 [SMILES: c1ccc(-c2ccnc3c2ccc2c(-c4ccccc4)ccnc23)cc1]

BPhen

TABLE 1

Test results of device examples and device comparative example 1

| No. | ET material | Drive voltage (V) | Efficiency EQE/% | E/CIEy |
|---|---|---|---|---|
| Device Example 1 | ET002 | 3.72 | 6.78% | 72.5 |
| Device Example 2 | ET026 | 3.76 | 6.92% | 74.0 |
| Device Example 3 | ET035 | 3.71 | 7.01% | 76.8 |
| Device Example 4 | ET048 | 3.80 | 6.80% | 73.1 |
| Device Comparative Example 1 | BPhen | 4.08 | 5.83% | 62.4 |

As can be seen from the above Table 1, compared with Device Comparative Example 1, the driving voltages of the light-emitting devices adopting the compound of the present disclosure are reduced by about 20%; the current efficiencies are increased by about 20%. It indicates that the structure of the compound according to the present disclosure can better interact with the dopant, preventing excitons from migrating towards the electron transmission side. Therefore, the electron mobility and the overall efficiency of the light-emitting device are improved.

Yet another aspect of the present disclosure also provides a display apparatus including the organic light-emitting display panel as described above.

Figure 3:
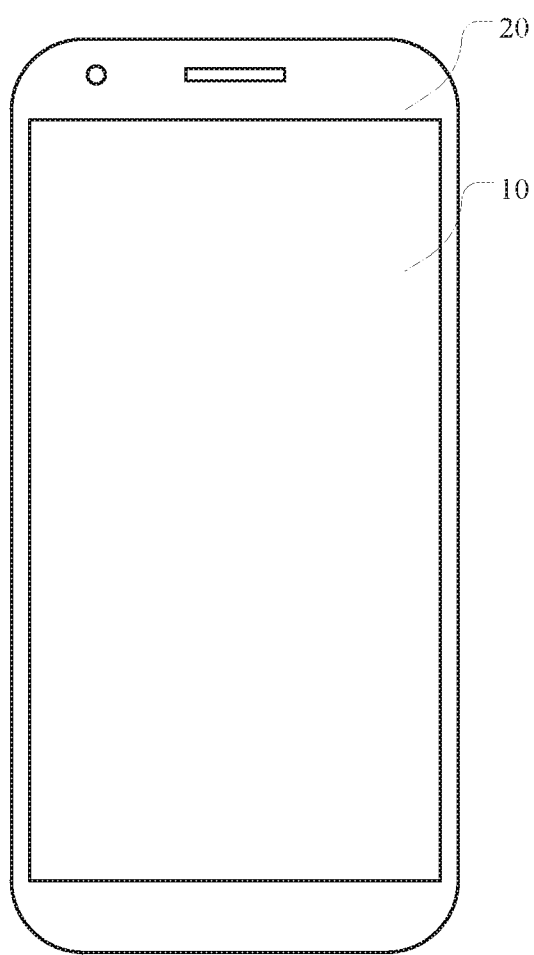
FIG. 3 is a schematic diagram of a display apparatus according to an embodiment of the present disclosure.

In the present disclosure, the organic light-emitting device can be an OLED used in an organic light-emitting display apparatus. The organic light-emitting apparatus can be a mobile phone display screen, a computer display screen, a liquid crystal television display screen, a smart watch display screen, or a smart car display panel, VR or AR helmet display screen, or display screens of various smart devices. FIG. 3 is a schematic diagram of a display apparatus according to an embodiment of the present disclosure, in which a smart mobile phone is denoted with reference number 20. In FIG. 3, the display apparatus includes the display panel 10 provided by the present disclosure.

The above embodiments of the present disclosure are several preferred embodiments, but not intended to limit the scope of the claims. Any change and modification can be made by those skilled in the art without departing from the scope of the present application, and the protection scope is defined by the claims.

What is claimed is:

1. A compound, having a general structure according to [Chemical Formula 1]:

[Chemical Formula 1]

$(A)_m$—$(L)_n$—$(B)_p$;

wherein A has a structure according to [Chemical Formula 2-1] or [Chemical Formula 2-2]:

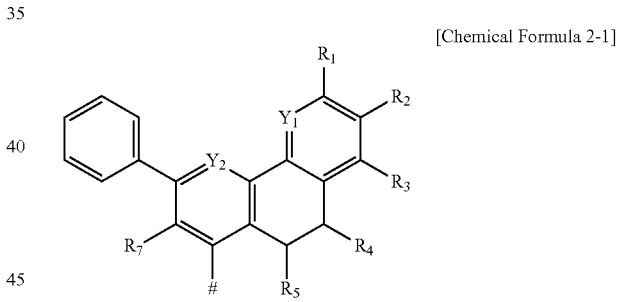

[Chemical Formula 2-1]

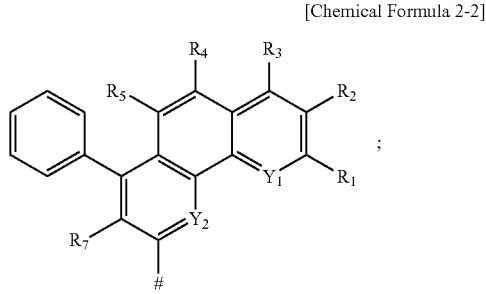

[Chemical Formula 2-2]

B has a structure according to [Chemical Formula 3-1] or [Chemical Formula 3-2]:

[Chemical Formula 3-1]

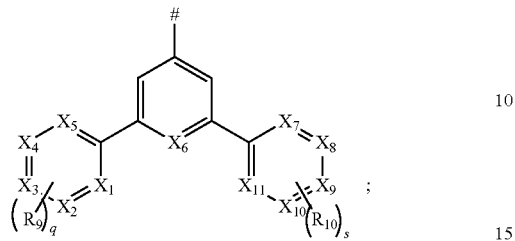

[Chemical Formula 3-2]

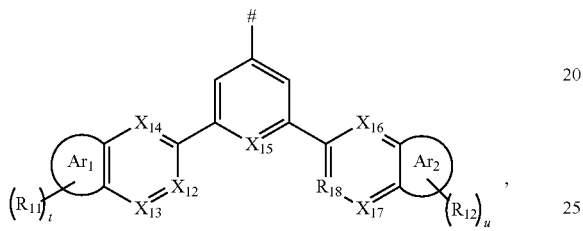

L is selected from the group as follows:

Chemical Formula 3-1

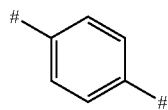

Chemical Formula 3-2

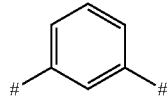

Chemical Formula 3-3

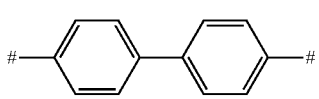

Chemical Formula 3-4

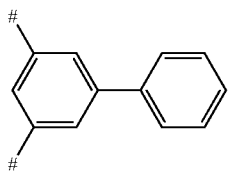

Chemical Formula 3-5

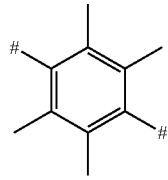

Chemical Formula 3-6

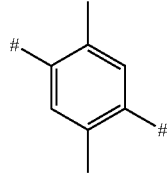

-continued

Chemical Formula 3-7

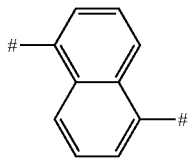

Chemical Formula 3-8

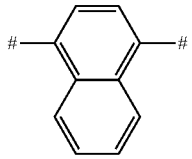

Chemical Formula 3-9

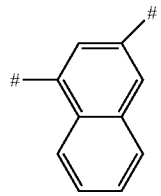

Chemical Formula 3-10

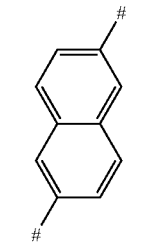

Chemical Formula 3-13

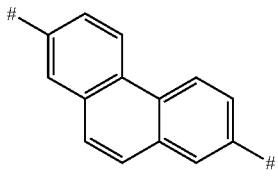

Chemical Formula 3-14

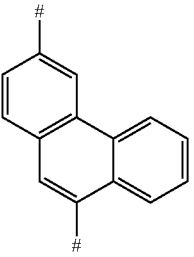

Chemical Formula 3-17

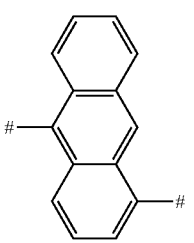

-continued

Chemical Formula 3-18

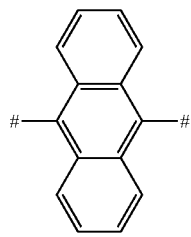

Chemical Formula 3-19

Chemical Formula 3-20 q, s, t and u are each an integer independently selected from 1 or 2;
m, n and p are each an integer independently selected from 1 or 2;
in the above [Chemical Formula 2-1] or [Chemical Formula 2-2], $Y_1$ and $Y_2$ are each independently a nitrogen atom; and $R_1$ to $R_5$ and $R_7$ are each independently a hydrogen atom or benzyl;
$R_9$-$R_{12}$ are each independently hydrogen, or pyridyl;
in the above [Chemical Formula 3-1], $X_1$-$X_5$ are each independently a carbon atom or a nitrogen atom, and only one of $X_1$-$X_5$ is a nitrogen atom, $X_6$ is a carbon atom; and $X_7$-$X_{11}$ are each independently selected from a carbon atom and a nitrogen atom, and only one of $X_7$-$X_{11}$ is a nitrogen atom;
in the above [Chemical Formula 3-2], $X_{12}$-$X_{14}$ are each independently a carbon atom or a nitrogen atom, only one of $X_{12}$-$X_{14}$ is a nitrogen atom, $X_{15}$ is a carbon atom; $X_{16}$-$X_{18}$ are each independently selected from a carbon atom and a nitrogen atom, only one of $X_{16}$-$X_{18}$ is a nitrogen atom; and $Ar_1$ and $Ar_2$ are each a fused benzene ring; and
# indicates a bonding position.

2. The compound according to claim 1, wherein among $X_1$-$X_5$ and $X_7$-$X_{11}$, $X_2$ and $X_{10}$ are each a nitrogen atom, and $X_1$-$X_3$-$X_5$, $X_7$-$X_9$ and $X_{11}$ are each a carbon atom.

3. The compound according to claim 1, wherein among $R_1$-$R_5$ and $R_7$, $R_3$ is benzyl, and $R_1$, $R_2$, $R_4$, $R_5$ and $R_7$ are each independently a hydrogen atom.

4. The compound according to claim 1, wherein L is any one of the following groups:

Chemical Formula 3-1

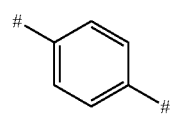

Chemical Formula 3-2

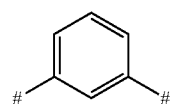

Chemical Formula 3-3

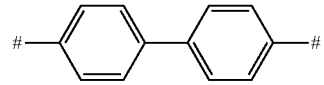

Chemical Formula 3-4

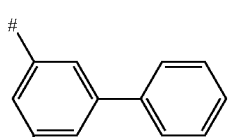

Chemical Formula 3-7

Chemical Formula 3-8

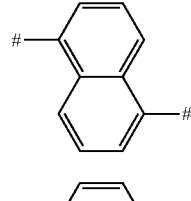

Chemical Formula 3-10

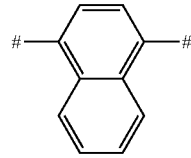

Chemical Formula 3-17

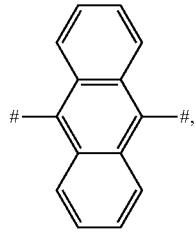

and
B is any one of the following groups:
[Chemical Formula 3-1]
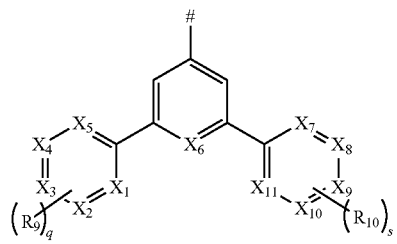
[Chemical Formula 3-2]
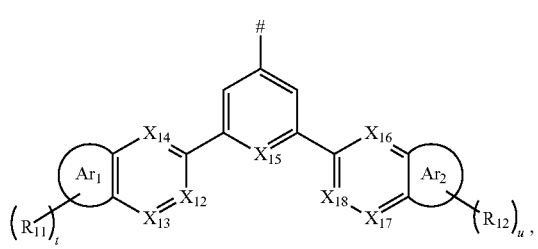
5. The compound according to claim 1, wherein the compound is selected from any one of the following compounds:
ET002
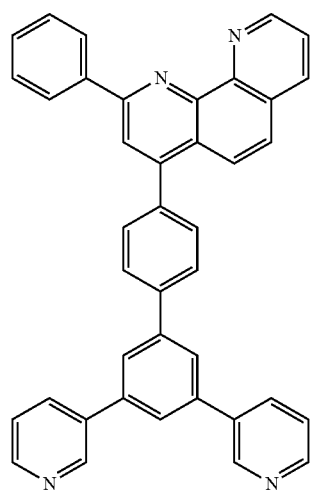
ET003
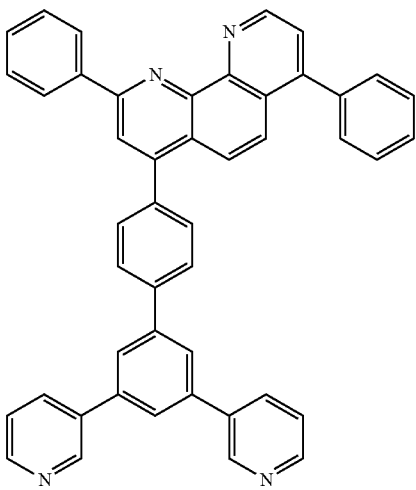
ET005
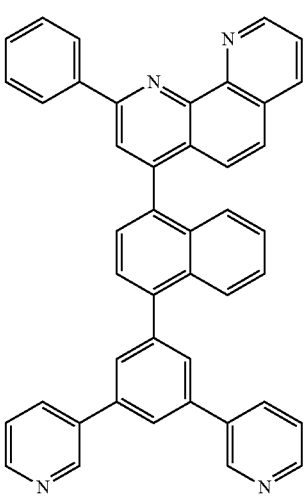
ET006
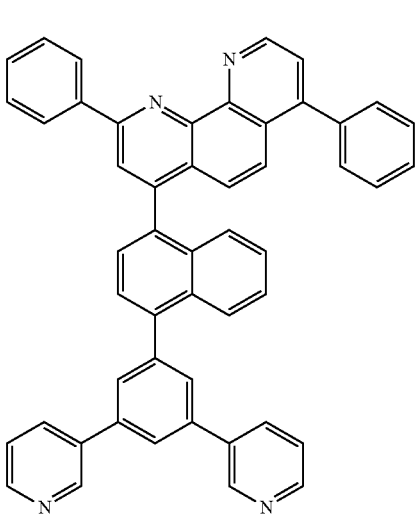

ET008
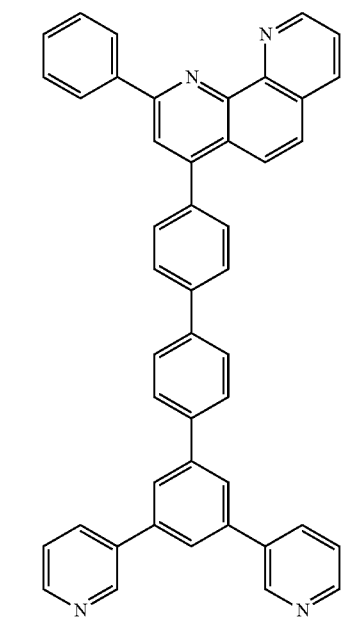
ET009
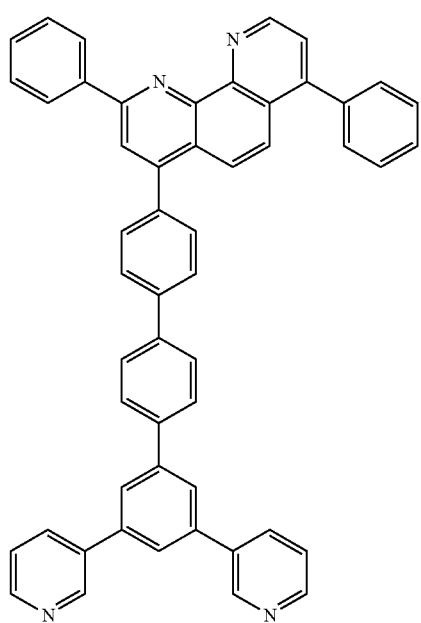
ET011
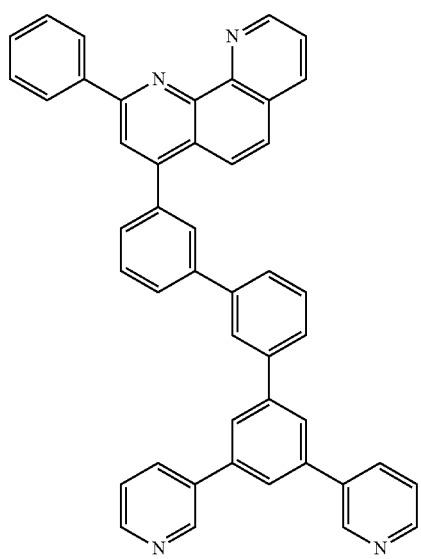
ET012
ET014
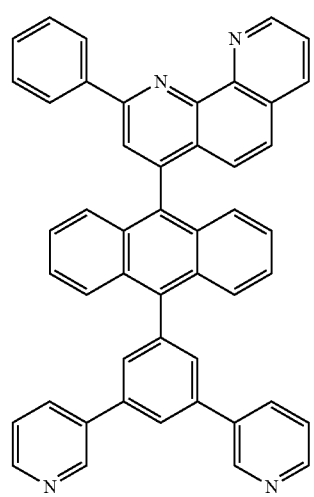

ET015
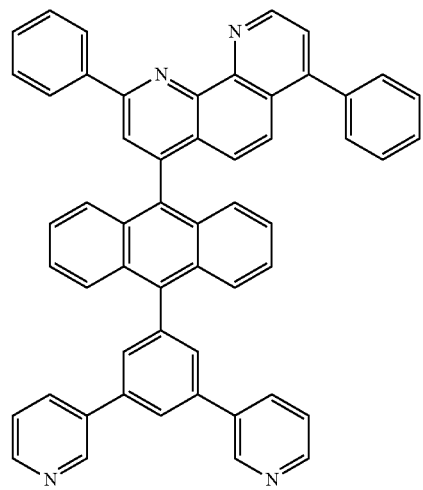
ET017
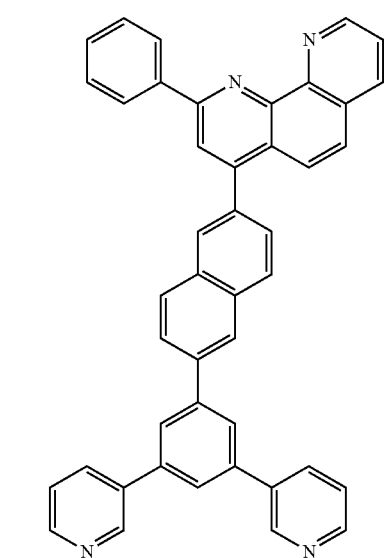
ET018
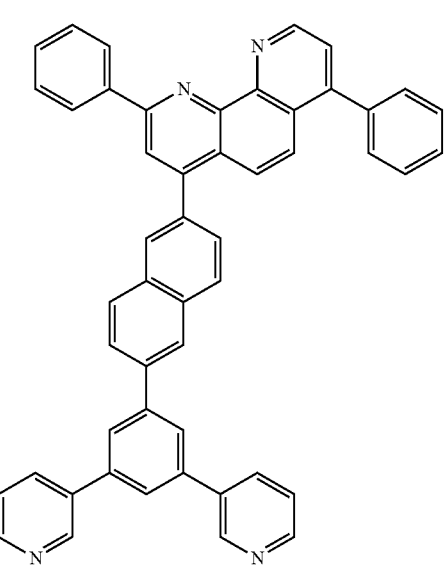
ET020
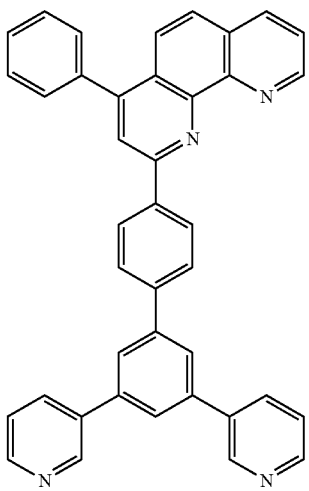
ET021
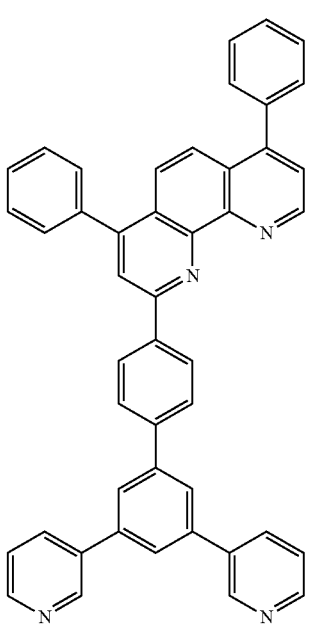
ET023
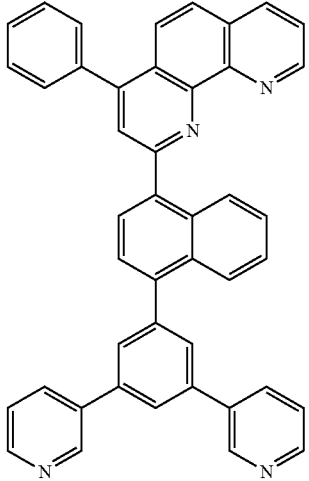

ET024
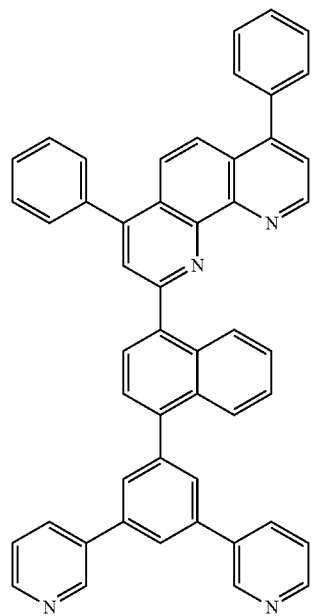
ET027
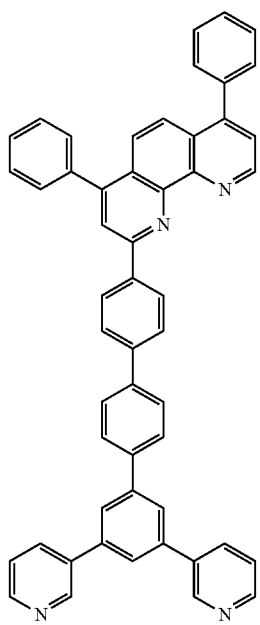
ET026
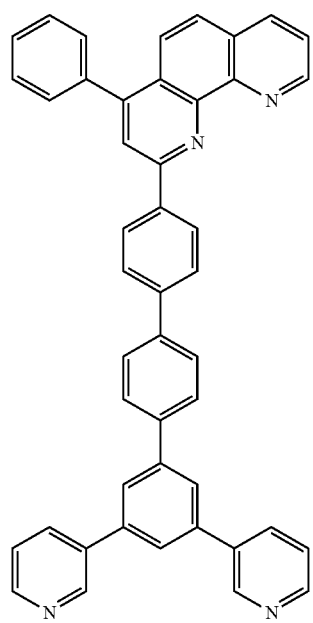
ET029
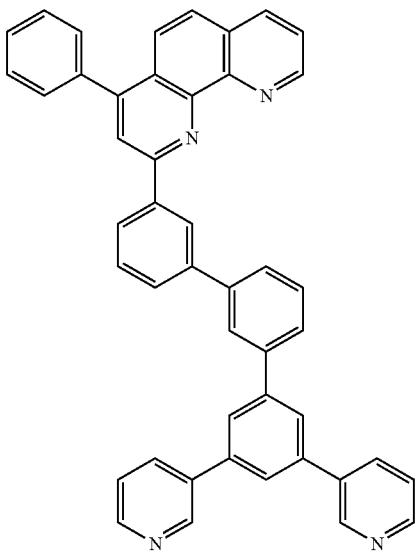

ET030
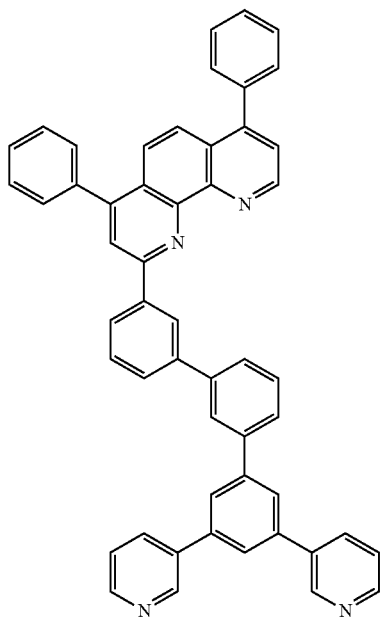
ET032
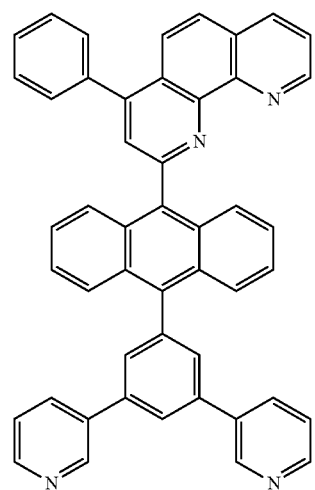
ET033
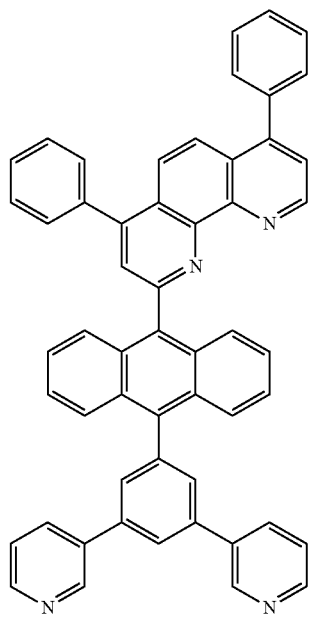
ET035
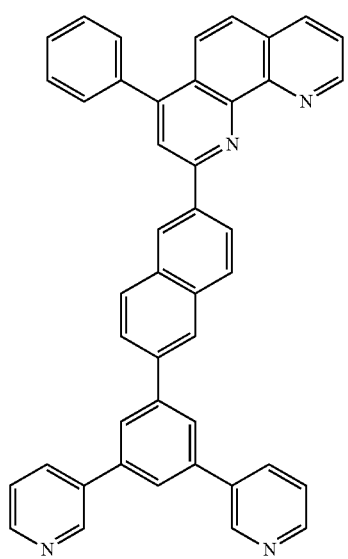

ET036
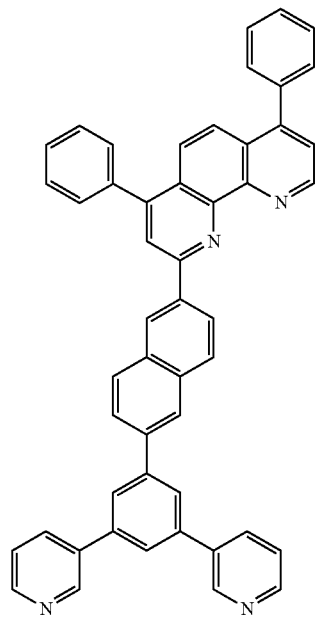
ET037
ET038
ET039
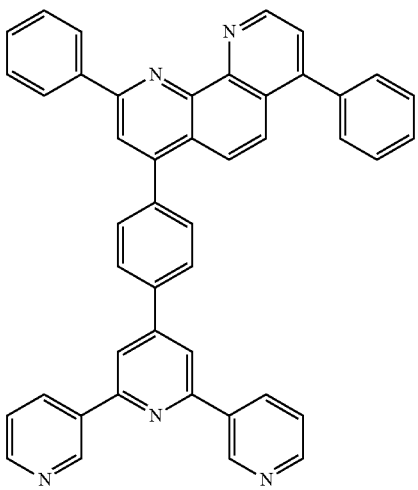
ET040
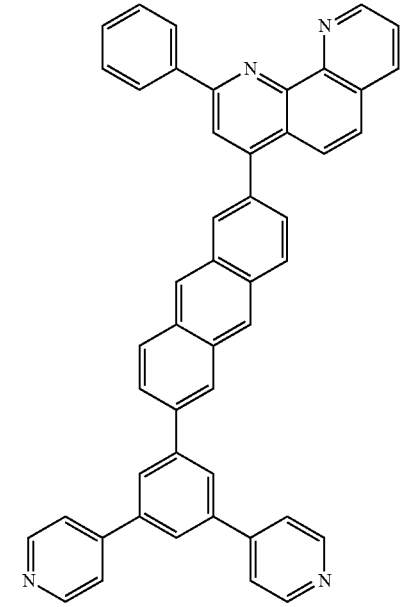

ET042
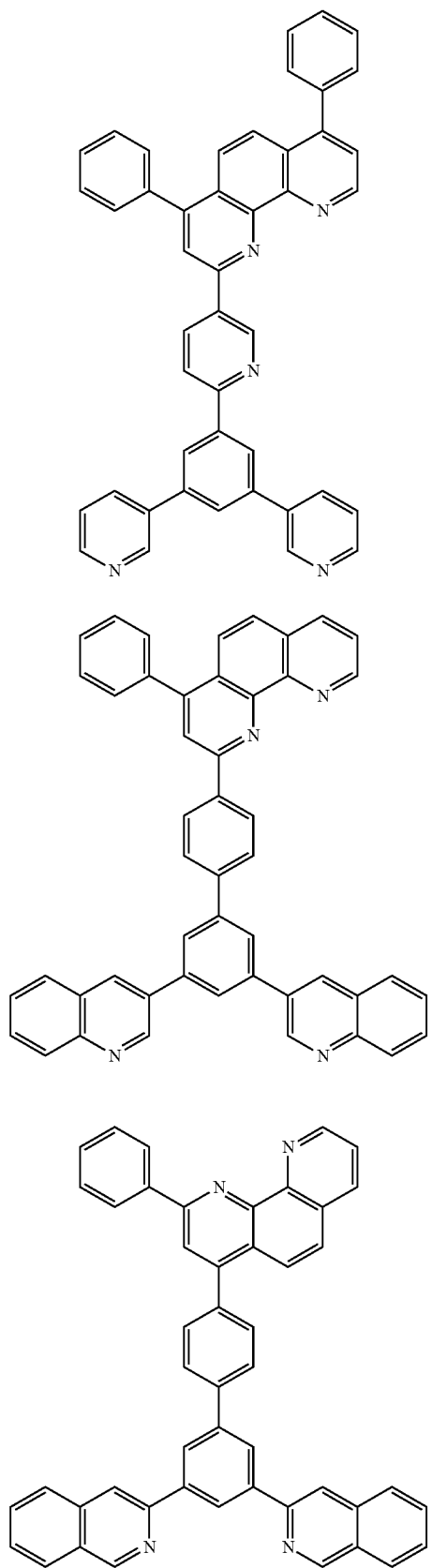
ET049
ET050
ET056
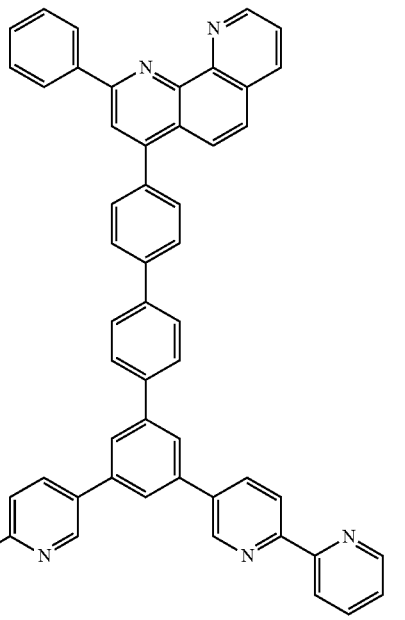
ET057
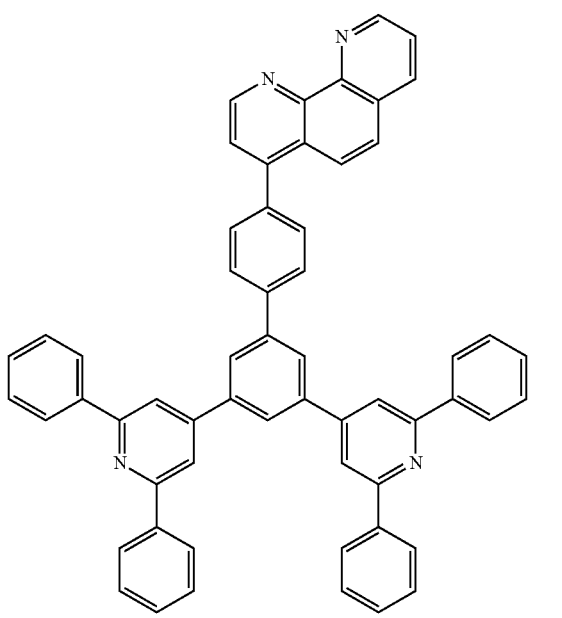

-continued

ET058

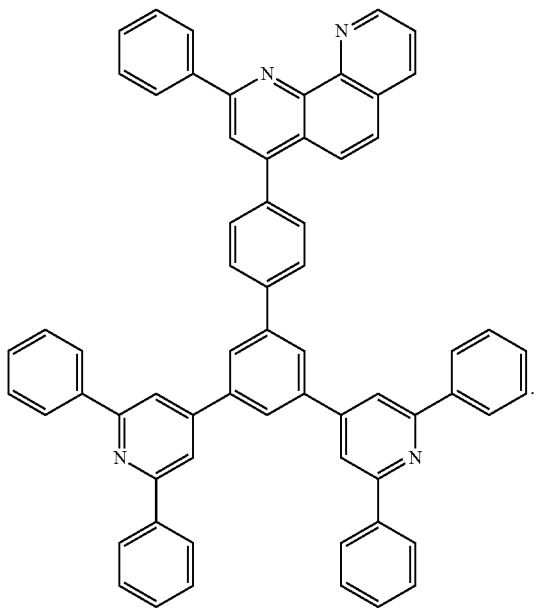

6. The compound according to claim 1, wherein the compound has a glass transition temperature greater than or equal to 120° C.

7. A display panel, comprising an organic light-emitting device, wherein the organic light-emitting device comprises an anode, a cathode opposite to the anode, an electron transmission layer, an electron injection layer, and a light-emitting layer that are disposed between the anode and the cathode, wherein a material of the electron transmission layer and/or a material of the electron injection layer comprise one or more of compounds according to claim 1.

8. The display panel according to claim 7, wherein an energy level difference between a lowest unoccupied molecular orbital (LUMO) energy level value of a material of the electron transmission layer and a LUMO energy level value of a material of the light-emitting layer or the electron injection layer is smaller than 0.2 eV; and a highest occupied molecular orbital (HOMO) energy level of the material of the electron transmission layer is at least 0.3 eV higher than a HOMO level value of the material of the electron injection layer.

9. The display panel according to claim 8, wherein the electron injection layer further comprises a doped metal.

10. The display panel according to claim 9, wherein the doped metal is selected from the group consisting of sodium, potassium, calcium, cesium, ytterbium, and combinations thereof.

11. The display panel according to claim 9, wherein a content of the doped metal in the electron injection layer is 1 wt % to 5 wt %.

12. The display panel according to claim 9, wherein a content of the doped metal in the electron injection layer is 3 wt %.

13. A display apparatus comprising the display panel according to claim 7.

* * * * *